United States Patent [19]
McGee et al.

[11] Patent Number: 5,855,592
[45] Date of Patent: Jan. 5, 1999

[54] SYSTEMS AND METHODS FOR MULTI-SITE CARDIAC DEFIBRILLATION USING MULTIPLE ELECTRODE STRUCTURES

[75] Inventors: David McGee, Sunnyvale; David K Swanson, Mountain View; James G Whayne, Saratoga, all of Calif.

[73] Assignee: EP Technologies, Inc., San Jose, Calif.

[21] Appl. No.: 842,491

[22] Filed: Apr. 24, 1997

[51] Int. Cl.[6] ....................................... A61N 1/39

[52] U.S. Cl. ............................... 607/4; 600/374

[58] Field of Search .................... 600/374, 518; 607/5

[56] References Cited

U.S. PATENT DOCUMENTS 5,269,298  12/1993  Adams et al. ................................ 607/5
5,494,042  2/1996  Panescu et al. ......................... 600/374

*Primary Examiner*—Scott M. Getzow
*Attorney, Agent, or Firm*—Lyon & Lyon LLP

[57] ABSTRACT

Systems and methods achieve defibrillation of a heart tissue region without resort to drugs or a painful electrical shock. The systems and methods sense electrical activity in the heart tissue region and generate an organization-indicating output. The organization-indicating output varies in relation to organization of heart rhythm in the heart tissue region. Use of the organization-indicating output guides the physician in organizing and entraining the heart tissue region.

108 Claims, 12 Drawing Sheets

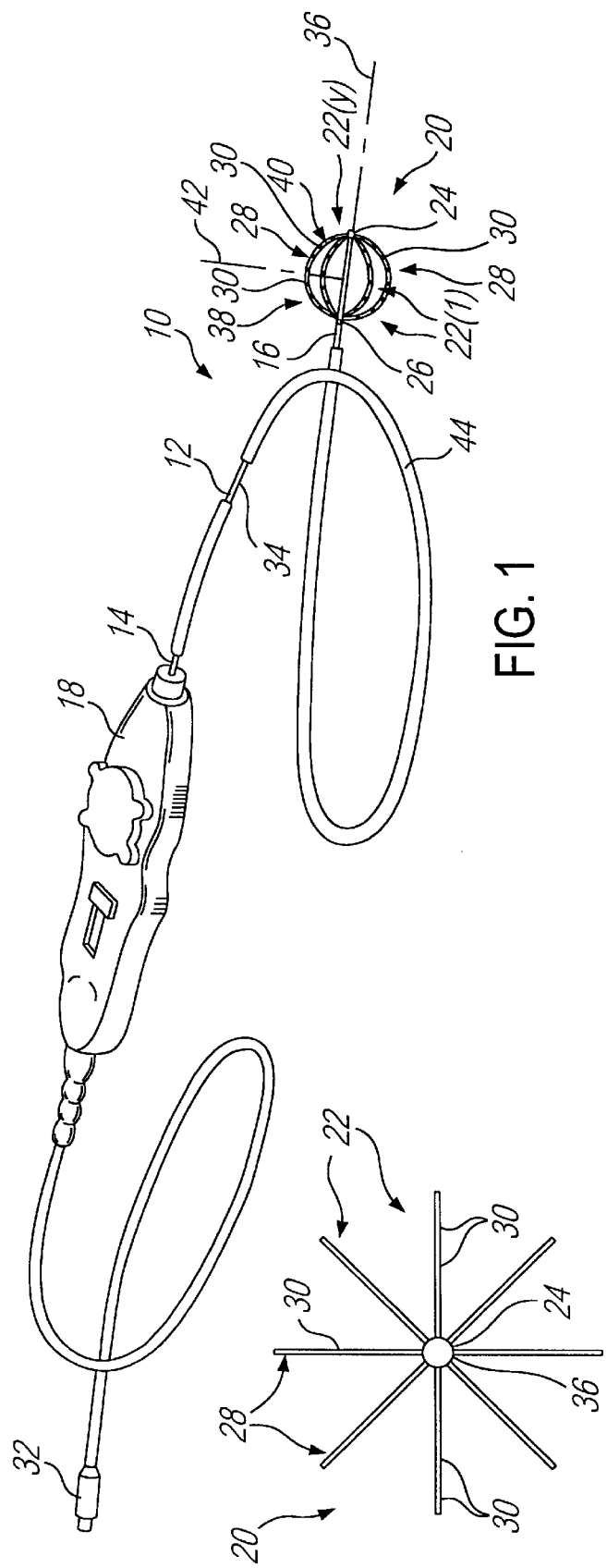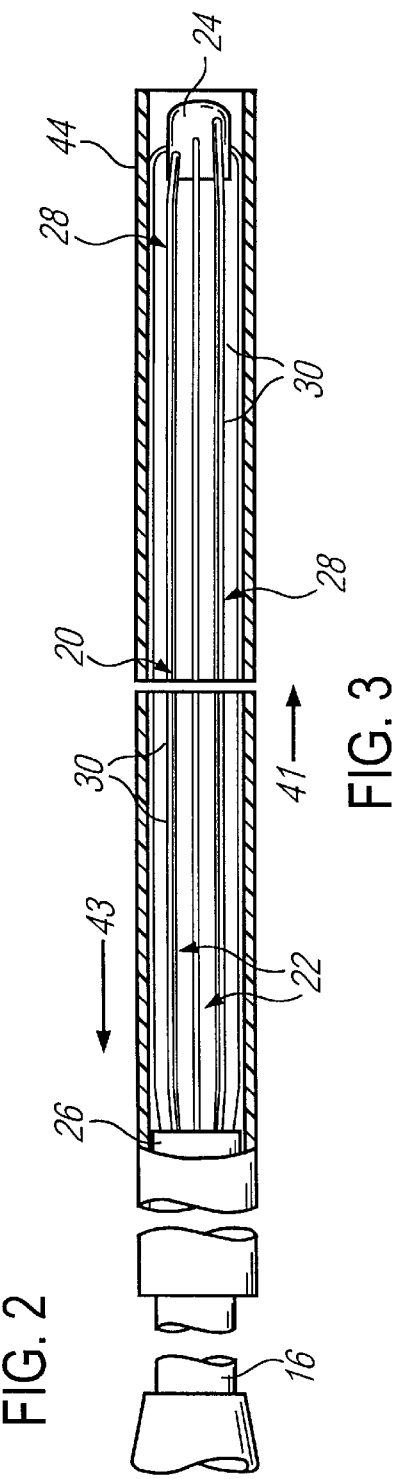

SYSTEMS AND METHODS FOR MULTI-SITE CARDIAC DEFIBRILLATION USING MULTIPLE ELECTRODE STRUCTURES

FIELD OF THE INVENTION

The invention relates to multiple electrode structures deployed in interior regions of the heart for diagnosis and treatment of cardiac conditions.

BACKGROUND OF THE INVENTION

Patients with ventricular fibrillation (VF) face immediate death (within minutes), if a defibrillation shock is not delivered soon after VF is detected.

One conventional defibrillation technique is to administer a defibrillation shock externally, using "paddles" or adhesive electrodes. Another conventional defibrillation technique is to administer a defibrillation shock internally, using intracardial electrodes carried by catheters, also called "internal cardioversion."

Because blood pressure drops immediately after VF occurs, the patient begins to lose consciousness within seconds after VF starts. Thus automatic implantable defibrillator shocks are often delivered to an unconscious or only partially conscious patient. Even so, shocks are painful and very disagreeable for these patients. Most patients tolerate these devices, because the alternative is nearly certain death. Although it is not well publicized, some patients do chose to have their devices inactivated, i.e. they chose to die rather than experience repeated shocks to save their lives.

Atrial fibrillation (AF) in humans, once induced for diagnostic reasons or occurring spontaneously, is often difficult to terminate. AF can also be converted to normal sinus rhythm using defibrillation shocks. Research suggests that defibrillation shocks administered to the atria can be painful to the patient if the delivered energy per pulse is greater than 1–1.5 Joules. The research also indicates that (at least with existing lead/pulse designs) defibrillation efforts are often ineffective unless energy pulses higher than 1 Joule are required. Thus, convention defibrillation of AF is often accompanied by moderate-to-intense pain for the patient.

In contrast to VF, the onset of AF, except in rare cases, does not cause immediate death. Instead, atrial fibrillation causes a long-term increased risk of death or stroke. Therefore, treatment for atrial fibrillation is usually not urgent. Restoring sinus rhythm or other organized rhythm within minutes or even hours is acceptable treatment for the vast majority of those patients.

For these reasons, delivering painful, disagreeable shocks automatically to these patients is harder to justify in the atrial defibrillation patient. Furthermore, in this patient population, the shock strengths that are required to defibrillate a patient are typically not well tolerated by an awake patient. Even partially sedated patients perceive the shocks as very painful, and typically will not willingly undergo multiple defibrillation shocks even in the controlled setting of the electrophysiological laboratory. When asked, patients candidly report that they can tolerate shocks at the rate of one per week to even one per year, with the tolerance level varying greatly among patients. To be widely tolerated, shock intensities need to be decreased substantially.

With convention defibrillation techniques, there is also a risk of induced ventricular fibrillation, possible unintended dislodgement of thrombus in one of the atria, and, in the case of internal cardioversion, the need to place one or more additional catheters within the heart.

An alternative conventional technique injects a bolus of an antiarrhythmic drug to attempt to convert the fibrillation to normal sinus rhythm. The disadvantages of this approach are low success rates and possible side-effects or reactions associated with the drug. The antiarrhythmic drug may also alter the heart's electrical functioning for a period of time, so that an electrophysiological study of the arrhythmic episode must be either delayed or canceled.

All these considerations surrounding conventional defibrillation techniques must be taken into account when the physician would like to induce and then terminate AF numerous times in an effort to gather information that would guide subsequent therapy.

Another technique being developed to defibrillate a patient in AF involves administering one or more defibrillation pulses (shocks) internally via one or more lead/electrode systems connected to an implanted sensor/pulse generator device. This system is generically referred to as an atrial implantable defibrillator (which will be called in shorthand "AID").

The AID concept has a number of potential shortcomings. They include:

(i) Pain is still likely to be encountered whenever the AID discharges to apply a defibrillation shock greater than 1 Joule in intensity;

(ii) Battery life is a key consideration in determining the clinical viability of any implantable device. During the evolution of implantable ventricular defibrillators, it was demonstrated that many ventricular tachycardia (VT) episodes could be terminated by pacing rather than by the administration of a defibrillation shock. When it is possible, not only does this spare the patient the pain associated with the shock, it also conserves battery life since (in the ventricular situation at least) a pacing train requires significantly less energy than a defibrillation shock. These facts have made possible implantable ventricular defibrillators that offer both longer battery life and reduced size.

(iii) There is always a possibility that a shock administered in an attempt to defibrillate the atria may inadvertently cause ventricular fibrillation. Although the likelihood of this event may be minimized by controlling the timing of the shock relative to the cardiac cycle, it may not be possible to entirely eliminate the risk. AID's currently do not have backup ventricular defibrillation capability.

SUMMARY OF THE INVENTION

This invention achieves defibrillation of a heart tissue region without resort to drugs or a painful electrical shock.

One aspect of the invention provides systems and methods for assessing organization of heart rhythm in heart tissue. The systems and methods sense electrical events in a heart tissue region and provide a sensed output. The systems and methods analyze the sensed output according to prescribed criteria and generate an organization-indicating output. The organization-indicating output varies in relation to organization of heart rhythm in the heart tissue region. Use of the organization-indicating output aids a physician in organizing and entraining heart tissue regions, without drugs or painful electric shocks.

In one embodiment, the organization-indicating output is characterized by a geometric form that varies in relation to organization of heart rhythm in the heart tissue region. The geometric form can, for example, include a plot of values derived from electrical events sensed in the heart tissue region. The plot can include a strange attractor that varies in geometric form in relation to organization of heart rhythm in the heart tissue region.

In one embodiment, the systems and methods employ a spaced apart array of electrodes to monitor electrical events at spaced-apart areas in the heart tissue region, from which organization-indicating output is generated. This aspect of the invention allows the physician to spatially organize and entrain relatively large heart tissue regions, such as an entire atrium. In an embodiment, the systems and methods hold multiple electrodes in contact with the interatrial septum, which experience has shown to be a junction for the propagation of atrial fibrillation wavelets.

For example, in one embodiment, the systems and methods deliver pacing pulses having selected pulse characteristics to a heart tissue region, while sensing electrical events and providing a sensed output to generate the organization-indicating output. The systems and methods alter the pulse characteristics to seek entrainment of the region, in reliance, at least in part, upon information obtained from the organization-indicating output.

Another aspect of the invention provides iterative systems and methods for entraining a heart tissue region.

In one embodiment, the systems and methods hold an array of electrodes in association with a heart tissue region, while operating in a local pacing mode. The local pacing mode delivers pacing pulses to a first number of the electrodes, less than all the electrodes, to entrain a localized area within the heart tissue region. The systems and methods also operate in successive, more global pacing modes. The successive pacing modes deliver pacing pulses to a successively greater number of the electrodes to entrain a successively larger area about the localized area.

In another embodiment, the systems and methods deliver pacing pulses to a first number of the electrodes to entrain a first localized area within the heart tissue region. The systems and methods also deliver pacing pulses to a second number of the electrodes to entrain a second localized area within the heart tissue region. In this embodiment, the systems and methods merge the first and second localized areas into a combined area to entrain a larger area in the heart tissue region.

In an embodiment, the systems and methods generate organization-indicating outputs relating to the organization of electrical events sensed in the targeted heart tissue areas. The systems and methods alter the pulse characteristics of the delivered pacing pulses, based, at least in part, upon the organization-indicating outputs.

According to another aspect of the invention, at least partial organization of a heart tissue region by any of the systems and methods above described makes possible the use of much lower shock intensities to restore normal rate rhythm. According to this aspect of the invention, the systems and methods assess variations of the organization-indicating output over time. The systems and methods generate a status output when improvement in the organization of heart rhythm in a localized heart tissue area is assessed. The systems and methods deliver a low level defibrillation pulse of less than 1 Joule to the entire targeted heart tissue region when the status output for the localized area is generated.

Another aspect of the invention provides systems and methods for identifying a candidate ablation site in heart tissue. The systems and methods hold a multiple electrode structure along a localized path in association with a heart tissue region subject to fibrillation. The systems and methods deliver pacing pulses only along the localized path, while sensing electrical events along the localized path. The systems and methods generating a candidate ablation site-identification output, when defibrillation is sensed to occur along the localized path as a result of the pacing pulses. In one embodiment, the systems and methods generate an organization-indicating output, as above described, to aid in candidate ablation site identification.

In various embodiments, the invention provides multi-site pacing signals from a three-dimensional array of electrodes within one or both atria. The multi-site pacing signals transmitted by the three-dimensional electrode array defibrillates AF, without the application of a high energy defibrillation shock. The pacing signals, simultaneously applied to a large area of one or both atria, entrain all or a large portion of the atria, so that atrial fibrillation cannot be sustained. Alternatively, one or both atria can be entrained by pacing electrodes located over a large area using the same pacing rate at all electrodes, but applying pacing signals from different electrodes at different times. Once pacing is terminated, normal sinus rhythm (driven by the SA node) takes over.

Another aspect of the invention provides an implantable system comprising an implantable sensor/processor/stimulator device coupled in association with a three-dimensional grid of electrodes. The electrode grid spans a majority of a selected one or more atria. The electrode grid is adapted to transmit prescribed pacing signals simultaneously to defibrillate AF without applying a high energy defibrillation shock.

Various aspects of the invention provide a three-dimensional array of multiple electrodes to defibrillate, promising greater defibrillation success rates.

The use of multiple low-energy pacing pulses rather than a defibrillation shock to defibrillate the atria results in several advantages. First, the patient should not experience pain related to the "defibrillation" since a shock is not used (conventional pacing typically does not produce pain). Second, because low energy pacing pulses replace high energy shocks, substantially less energy is required to defibrillate a given arrhythmic event. If so, this may lead to implantable devices that offer a combination of longer battery life and reduced device size. Third, because delivery of a high energy defibrillation shock is not involved, the likelihood of an induced ventricular fibrillation is diminished, particularly in a heart having reasonably normal AV conduction (i.e.,"normal" AV node function, no accessory pathways, etc.).

The various features and advantages of the inventions are set forth in the following Description and Drawings, as well as in the appended Claims.

BRIEF DESCRIPTION OF THE DRAWINGS

FIG. 1 is a side view of a multiple electrode probe having an electrode support assembly that is both axially and radially symmetric when in its deployed condition;

FIG. 2 is an end view of the probe shown in FIG. 1;

FIG. 3 is an enlarged side section view of the distal end of the probe shown in FIG. 1, showing the associated electrode support assembly in a collapsed condition within a sliding outer sleeve;

Figure 4:
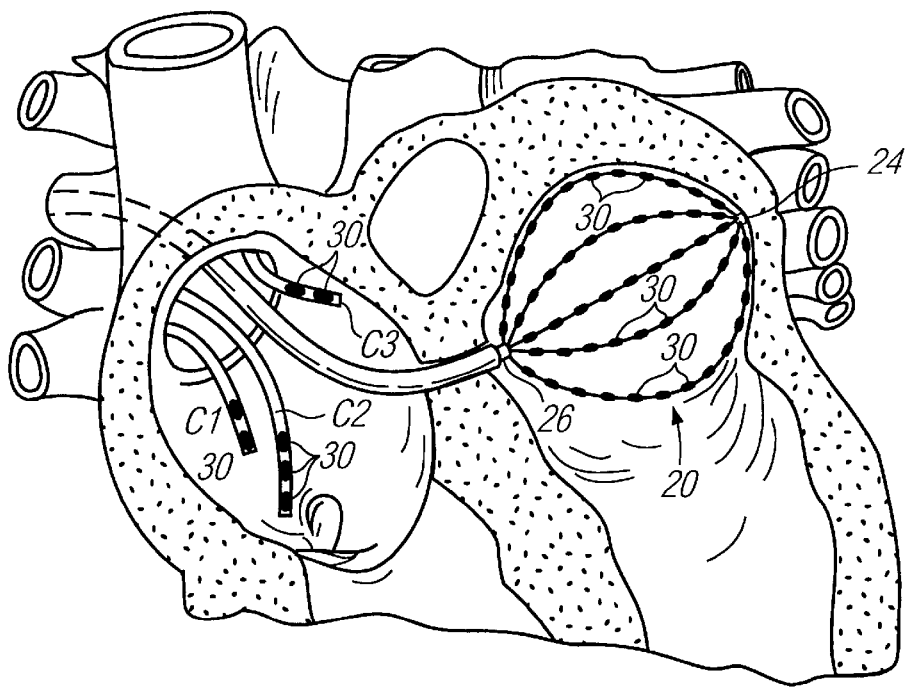
FIG. 4 is an enlarged, somewhat diagrammatic view, of the multiple electrode probe deployed transeptally in the left atrium of a heart.

The invention may be embodied in several forms without departing from its spirit or essential characteristics.

DESCRIPTION OF THE PREFERRED EMBODIMENTS

FIG. 1 shows a multiple electrode probe 10. The probe 10 includes a flexible catheter tube 12 with a proximal end 14 and a distal end 16. The proximal end 14 carries an attached handle 18. The distal end 16 carries a three-dimensional electrode support assembly 20, shown in side view in FIG. 1 and in top view in FIG. 2.

As FIGS. 1 and 2 show, the support assembly 20 comprises an array of flexible spline elements 22. Each spline element 22 preferably comprises a flexible body made from resilient, inert wire or plastic. Elastic memory material such as nickel titanium (commercially available as NITINOL™ material) can be used. Resilient injection molded plastic or stainless steel can also be used.

The spline elements 22 extend longitudinally between a distal hub 24 and a base 26. The base 26 is carried by the distal end 16 of the catheter tube 12. As FIGS. 1 and 2 show, each spline 22 is preformed with a convex bias, creating a normally open three-dimensional basket structure expanded about a main center axis 36.

The probe 10 also includes an electrode circuit assembly 28, one for each spline 22. Each circuit assembly 28 comprises an array of multiple electrodes 30. The electrodes 30 can comprise solid rings, coils, deposited layers, alternate conducting structures, or any combination of such structures.

The electrodes 30 are electrically coupled by signal wires 34, which extend through the catheter tube 12, to the external connector 32, which the handle 18 carries (see FIG. 1). Further details of the construction of the electrode circuit assemblies are shown in pending U.S. application Ser. No. 08/206,414, filed Mar. 4, 1994, which is incorporated herein by reference.

In FIGS. 1 and 2, there are eight, radially and axially symmetric spline elements 22, each circumferentially separated by about 45°. Of course, other geometries employing more or fewer spline elements 22 and electrodes 30 can be used.

As FIG. 3 shows, in the illustrated and preferred embodiment, the probe 10 includes an outer sheath 44 carried about the catheter tube 12. The sheath 44 has an inner diameter that is greater than the outer diameter of the catheter tube 12. As a result, the sheath 40 slides along the catheter tube 12.

As FIG. 3 shows, forward movement (arrow 41 in FIG. 3) advances the slidable sheath 44 completely over the electrode support assembly 20. In this position, the slidable sheath 44 compresses and collapses the support assembly 20 into a low profile for introduction through a vein or artery to the intended treatment site within the body.

As FIG. 1 shows, rearward movement (arrow 43 in FIG. 3) retracts the slidable sheath 44 away from the support assembly 20. This removes the compression force. The freed support assembly 20 opens and assumes its three dimensional shape.

When deployed for use (as FIG. 4 shows), the support assembly 20 of the probe 10 holds the electrodes 30 in contact against the endocardium. According to the invention (see FIG. 4), the physician places the structure 20 in one or both atria, depending upon relevant clinical factors. FIG. 4 shows the structure 20 deployed transeptally in the left atrium. The structure 20 places a three-dimensional array of electrodes 30 in contact with a region of tissue spanning a majority of the atrium where the structure 20 is located.

Figure 5:
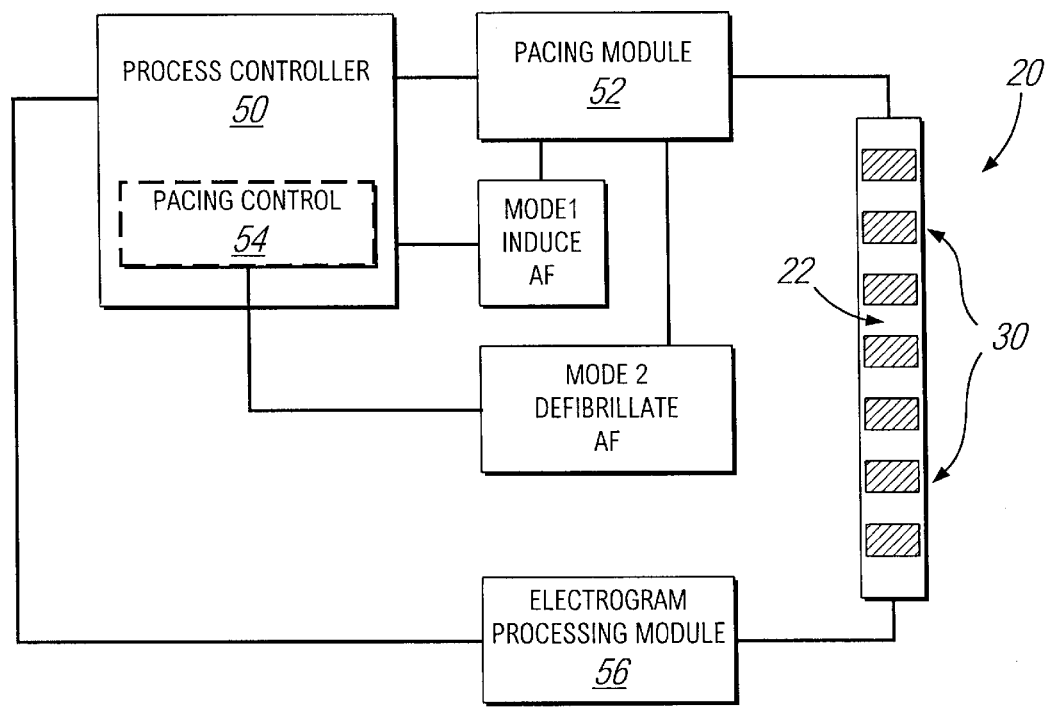
FIG. 5 is a block diagram, schematic view of a process controller associated with the multiple electrode probe shown in FIG. 1, the controller being adapted to command a first pacing mode to induce AF and a second pacing mode to defibrillate the AF.

The structure 20 is used in association with a process controller 50, shown in FIG. 5. A pacing module 52 is coupled to the process controller 50. The process controller 50 includes a pacing control algorithm 54 that commands the pacing module 52 to deliver pacing pulses from selected one or more multiple electrodes 30 on the support assembly 20. The pacing pulses can be delivered simultaneously by all electrodes 30. Alternatively, each electrode 30 can deliver a pacing pulse at a different time.

The pacing control algorithm 54 commands the pacing module 52 in at least two modes of operation. In a first mode, the algorithm 54 commands the module 52 to transmit to one or more electrodes 30 pacing signals having the current level and cycle length to purposely induce atrial fibrillation. Alternatively, the atrial fibrillation may be induced by another conventional programmed pacing technique.

The processor controller 50 also includes an electrogram processing module 56, which is coupled to the electrodes 30 on the structure 20. The electrogram processing module 56 receives the electrical events sensed by the electrodes 30 during atrial fibrillation. The processing module 56 creates electrograms based upon these signals for display and analysis by the physician.

The pacing control algorithm 54 also commands the pacing module 52 in a second mode to transmit to a selected one or more electrodes 30, or all the electrodes 30 at once, pacing signals having the current levels and cycle lengths to capture and defibrillate the induced atrial defibrillation. Although the second mode may employ sub-threshold pacing techniques, it is believed that current levels of the pacing signals transmitted during the second mode should be comparable to those normally used for conventional pacing. In any case, the pacing pulses transmitted during the second mode are characterized by a low energy level, several orders of magnitude less than the energy level of a conventional defibrillation shock pulse (which, to be effective, is typically higher than about 1.0 Joules).

In the second mode, the pacing pulses commanded by the pacing control algorithm 54 render all or a large portion of the atrium near the electrodes 30 refractory for a period of time long enough so that atrial fibrillation cannot be sustained. As a consequence, normal sinus rhythm (driven by the SA node) will take over once second mode pacing by the module 52 is terminated.

Previous pacing probes carry a relatively few number of electrodes. These electrodes can "capture" (via pacing) a small region surrounding the pacing site. However, capture in this localized region is typically not large enough to interrupt the arrhythmia. See, for example, Haffahee et al., "High Frequency Atrial Burst Pacing for Termination of Atrial Fibrillation", Abstract 34, *PACE,* Vol. 18, April 1995, Part II, which discloses the use of a conventional electrophysiological catheter having 2 to 4 electrodes arranged along the body of the catheter. Relatively poor defibrillation success rates are reported using this two-dimensional electrode arrangement.

On the other hand, the structure 20 establishes a three-dimensional grid of multiple electrodes 30. Under the command of the pacing control algorithm 54, the three-dimensional grid paces from electrodes 30 located in a substantially larger region of the atrium.

Pacing signals of a given cycle length may be simultaneously applied by all the electrodes 30. However, taking into account that atrial fibrillation cycles lengths vary in different regions of the atria, the pacing signals are preferably applied in a purposeful, iterative pattern from different electrodes 30 in different locations and at different times. In this embodiment (see FIG. 15), the pacing control algorithm 54 spatially organizes the atria by first selecting pacing characteristics that capture a localized atrial region. Once the localized atrial region is entrained, the pacing control algorithm expands the targeted atrial region beyond the local region and iteratively changes the pacing characteristics to organize the larger atrial region. Once the larger atrial region is entrained, the pacing control algorithm 54 again expands the targeted region and iteratively changes the pacing characteristics to capture the even larger region. The pacing control algorithm proceeds in this iterative basis, entraining a successively larger atrial region, until the desired entire atria region is entrained.

Capture occurring in this purposeful way ultimately calls into play a large, three-dimensional grid of electrodes, which, in time, render all or a larger portion of the atrium refractory. The induced arrhythmia is thereby interrupted.

The control processor 50 stores the pacing control algorithm 54 for execution to minimize operator effort. To provide widespread capture throughout the three-dimension grid of electrodes 30, the pacing control algorithm 54 applies to a selected electrode or a selected group of electrodes pacing pulses spanning at least one cardiac cycle (or at least a few seconds), with the pacing cycle length being faster than that used for normal pacing (e.g. 3 to 10 Hz). Of course, the pacing frequency might be different than the 3 to 10 Hz frequency range mentioned above. A single pulse might be sufficient. The local pacing characteristics can vary from electrode to electrode, and the pacing characteristics at each electrode can themselves change over time, depending upon the instant atrial fibrillation cycle length and the dimension of the atrial region targeted for capture.

The resulting patterns of pacing pulses, intended to defibrillate, occur somewhat faster that the local activation interval for the myocardium. As with entrainment mapping for monomorphic ventricular tachycardia (MVT), the local pacing rates established by the algorithm 54 need to be faster than the local heart rate of the tissue.

In operation, the algorithm 54 ultimately strives to pace-capture and entrain significant larger areas of tissue. To accomplish this objective, the algorithm 54 must take into account special conditions, which are operative in fibrillating atrial tissue, but which are not present in MVT. These special conditions include:

(i) the highly variable cycle lengths between activation sequences, mentioned above, which fibrillating tissue exhibits. MVT, on the other hand, exhibits relatively consistent cycle lengths between activation sequences.

(ii) Furthermore, the window of time during which the local heart tissue can be stimulated, called the "excitatory gap," tends to be shorter for fibrillating tissue than for MVT.

The control algorithm 54 can contend with these special conditions in various ways to locally entrain tissue at multiple sites.

In one embodiment, the algorithm 54 conditions the multiple electrodes in a selected heart region to provide electrograms. The algorithm 54 processes the electrograms to determine the cycle lengths $CL_{(1 \ to \ N)}$ for a selected, representative sample size (N) of local activation sequences. For example, 10 or more activation sequences can comprise a representative sample size (N).

From these data, the algorithm derives an average cycle length $CL_{AV(1 \ to \ N)}$ and cycle length variability $\Delta CL_{(1 \ to \ N)}$ for each electrode in the localized region. In general, it can be expected that both the average cycle length $CL_{AV(1 \ to \ N)}$ and cycle length variability $\Delta CL_{(1 \ to \ N)}$ will vary considerably among electrodes, even when long sampling times are used. Typical average cycle lengths $CL_{AV(1 \ to \ N)}$ for humans are 100 to 150 msec. The algorithm 54 retains this processed information in memory.

The algorithm 54 further processes the cycle length information for the localized region to determine the shortest average cycle length $MINCL_{AV(N)}$ for the sample size N. The algorithm determines the initial pacing rate $R_{PACE}$ as a function of the quantity $MINCL_{AV(N)}$, or:

$$R_{PACE} = f(MINCL_{AV(N)})$$

For example, the electrodes within the localized region, or a selected subset of the electrodes, are paced at $MINCL_{AV(N)}$ or at some selected fraction of $MINCL_{AV(N)}$, for example, 0.9 $MINCL_{AV(N)}$. $MINCL_{AN(N)}$ can be varied from electrode to electrode, and can be iteratively changed over time, as required to achieve capture.

The time of pacing can also be varied within the region selected for capture from electrode to electrode for the same purpose. Pacing at slightly different times at different electrodes reduces the peak current output requirement for the pacing module 52. For example, to pace at 5 mA through each of one hundred electrodes requires a relatively high current of 500 mA. On the other hand, offsetting the timing to pace through groups of ten electrodes at a time reduces the peak current requirement for each pulse cycle to a lower current magnitude of 50 mA. For example, by establishing a pace width at each electrode group of 1.0 msec, the pacing pulses could be delivered to all one hundred electrodes within a 10 msec period. This time period is about 10% of a cardiac cycle length during atrial fibrillation, and therefore an acceptable pacing scheme.

The algorithm 52 avoids higher total peak current amplitudes (i.e., approaching 1 A), which could occur with simultaneous pacing at each electrode, for other reasons. High peak current amplitudes could field-stimulate the ventricle, which could induce ventricular arrhythmia or ventricular fibrillation. In addition, unipolar pacing using lower peak current amplitudes (i.e., less than about 100 mA) also decreases the probability of stimulating the muscle tissue near the indifferent electrode.

In establishing the pacing sequence, the algorithm 54 also takes into account physiological constraints. For example, the pacing sequence established by the algorithm 54 takes into account the refractory nature of heart tissue, which prevents re-stimulation of myocardial tissue for a refractory period after each activation. The refractory period amounts to about 80 msec to about 120 msec for people in chronic atrial fibrillation. Applying pacing pulses during the refractory period is, at best, inefficient.

The algorithm 54 also takes into account the spacing between electrodes in the targeted entrainment region relative to the rate at which activation wavefronts move during fibrillation. The activation wavefront movement rate is typically at about 100 cm/sec. At this rate, the activation wavefront propagates about 1 cm from the pacing site in 10 msec. If two electrodes are 1 cm apart, the algorithm 54 preferably assures that the pacing pulses are delivered to each electrode within 10 msec of each other.

In one embodiment, the algorithm 54 establishes a proper pacing sequence by distributing pacing signals to electrodes in an order that takes into account the geometry of the electrode array, particularly as the entrainment area increases in size. For example, for a three-dimensional structure like that shown in FIG. 1, the algorithm 54 delivers the first set of pacing pulses to the band of most distal electrodes on each spline element, then proceeds in sequence to adjacent bands of electrodes in succession toward the most proximal band of electrodes on the spline elements. For example, for a structure having eight spline elements with eight electrodes on each spline element, and with stimulation pulses 1 msec wide, the algorithm 54 delivers pacing pulses to all 64 electrodes in as little as 8 msec.

Figure 15:
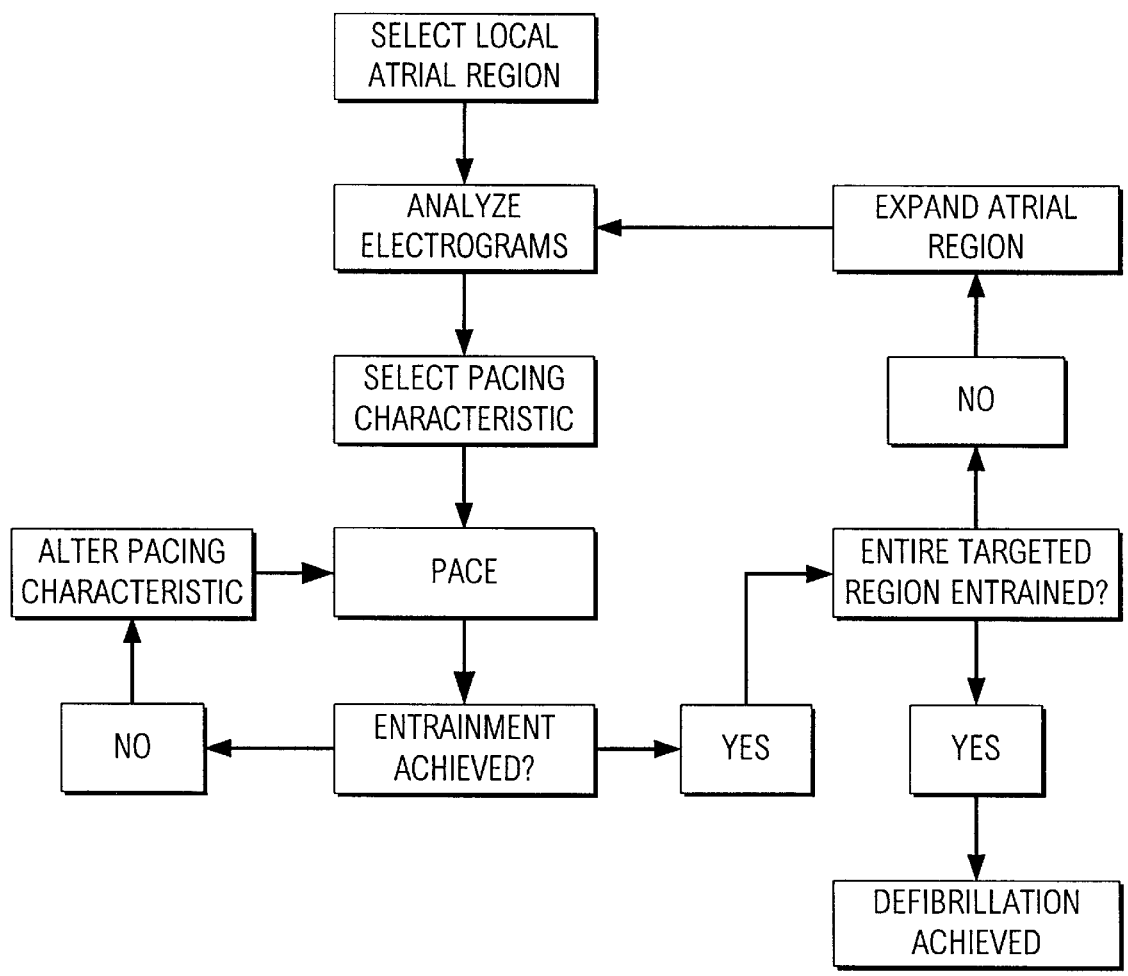
FIG. 15 is a flow chart showing an algorithm for defibrillating an atrial region using multiple electrodes.

As before described, and as FIG. 15 shows, once a selected localized region of atrial tissue is entrained, the algorithm 54 expands the boundaries of the selected tissue region to incorporate a larger atrial region. Based upon electrograms in this region, which involves a larger number of electrodes, the algorithm again determines the cycle lengths $CL_{(1\ to\ N)}$ for a sample size (N) of local activation sequences in the expanded region. Through iterative processing, the algorithm changes the pacing characteristics to achieve entrainment in the expanded region. This process is repeated, sequentially expanding the atrial region to spatially organize a progressively larger atrial region, until the targeted atrial region (which can comprise one or both atria) are entrained, depending upon the clinical objectives.

To assist in the organization of sequentially larger atrial regions, the control processor 50 includes a module 200 (see FIG. 21), which assesses the degree to which a targeted heart region has been organized by the algorithm 54. The targeted region analyzed by the module 200 can be localized (i.e., within a few mm of a particular electrode), or it can encompass both atria.

Figure 21:
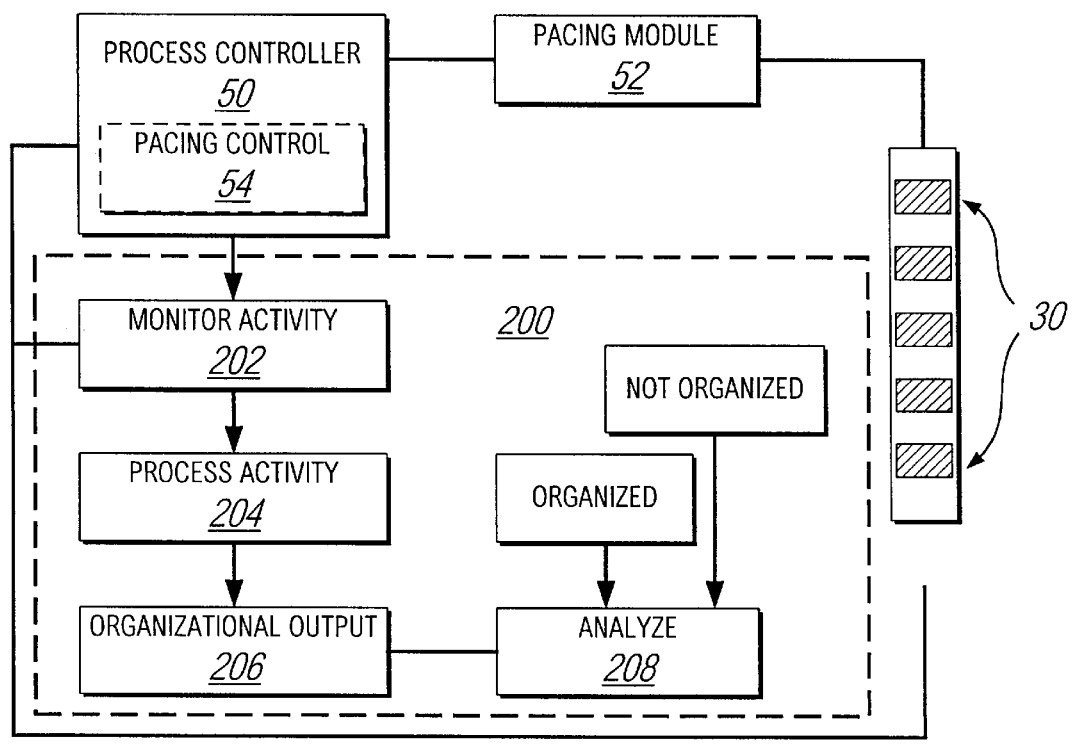
FIG. 21 is a block diagram, schematic view of a process controller associated with the multiple electrode probe shown in FIG. 1, the controller being adapted to assess the level of rhythm organization within tissue.

As FIG. 21 shows, the module 200 includes an element 202 to monitor activation times in the targeted region. A processing element 204 receives activation times from the monitor element 202 and generates an organization-indicating output 206. The output 206 can vary in its format. In a preferred embodiment, the output 206 comprises a phase plot, which changes in relation to the degree of organization.

Figure 16:
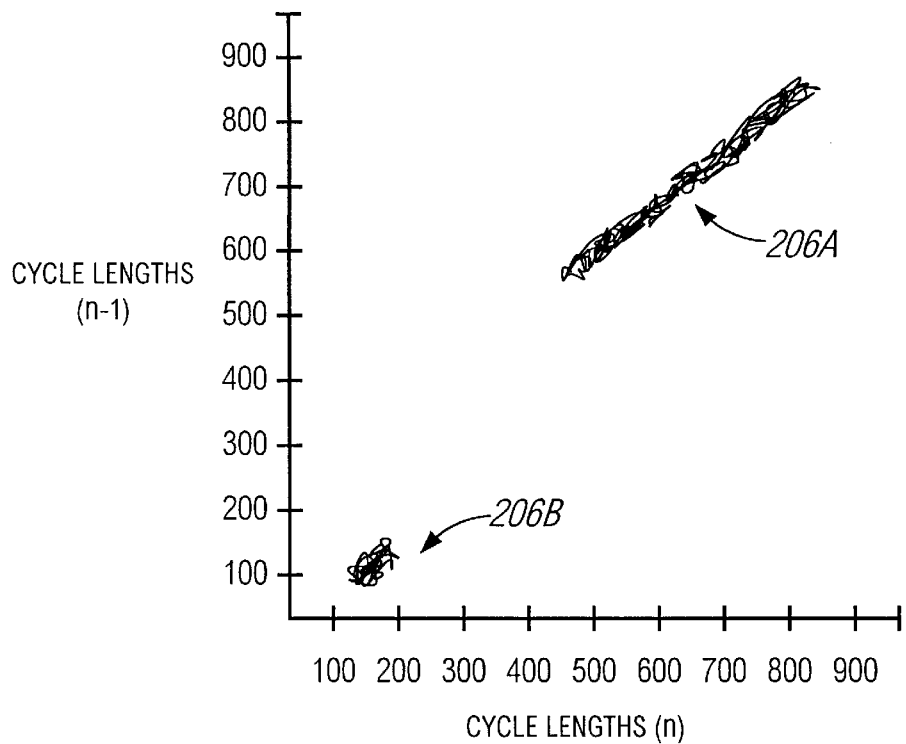
FIG. 16 are representative phase plots, taken over an extended period of time, of regions where organized and unorganized activation patterns occur, showing the difference in the strange attractors within the plots.

FIG. 16 shows first and second phase plots 206A and 206B, each constructed by the processing element 204, by plotting monitored cycle lengths of each recorded beat (n) versus the cycle length of the previous beat (n−1), over an extended period of time (i.e., over at least several minutes).

The first phase plot 206A in FIG. 16 is representative of a typical organized rhythm pattern. Organized rhythms have consistent cycle lengths from beat to beat at a single recording site, and also have the same cycle length for all recording sites. In phase plot 206A, almost all the data dots lay along a linear line, indicating that the cycle length for the previous beat (N−1) served as a good predictor of the cycle of the current beat (n).

The conglomeration of dots of the phase plot 206A will be called the "strange attractor," consistent with chaos theory. The phase plot 206A for an organized region is characterized by a small effective area for the strange attractor.

On the other hand, phase plot 206B in FIG. 16 is representative of a region where atrial fibrillation is occurring. Phase plot 206B shows that an unorganized region is characterized by a larger effective area for the strange attractor.

Figure 17:
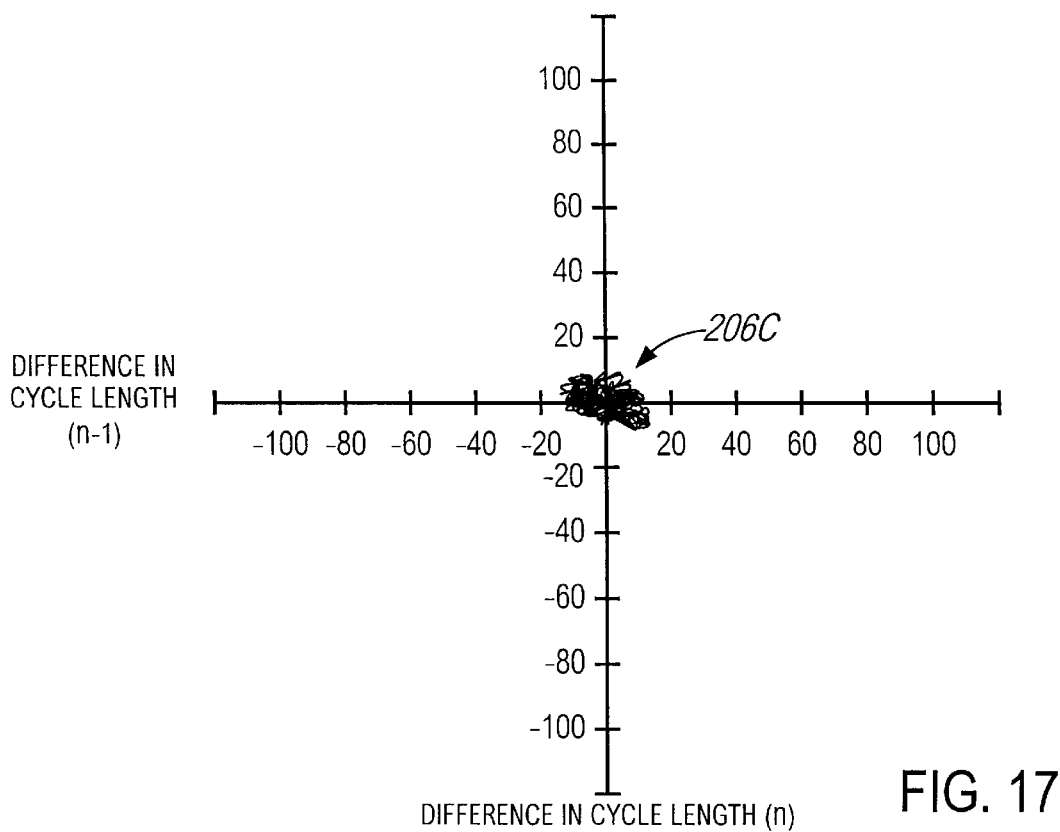
FIG. 17 is a representative phase plot containing a strange attractor, taken over a short period of time, of a region where organized activation patterns occur.

FIG. 17 shows a phase plot 206C for an organized rhythm, for a shorter sequence of 5 to 10 beats. To facilitate analysis, the average cycle length is subtracted out for all beat n and beat n−1 measurements of cycle lengths, and FIG. 17 plots the difference in cycle lengths (n) (x-axis) against the difference in cycle length (N−1) (y-axis). The resultant strange attractor for the shorter sequence of beats looks like a fuzzy dot centered around the average cycle length at the point 0,0.(i.e., at the intersection of the x-axis and y-axis), since an organized heart rate changes little during a short sequence of beats. Thus, the apparent size of the strange attractor for plot 206C is much smaller than that shown for plot 206A in FIG. 16.

Figure 18:
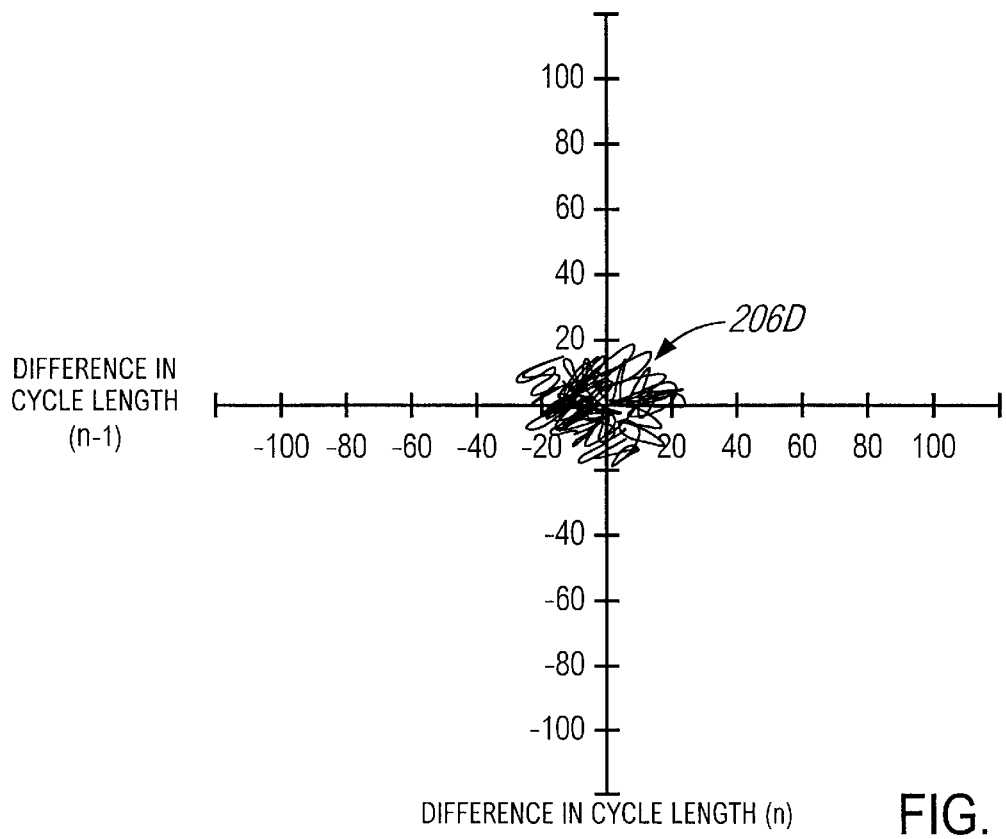
FIG. 18 is a representative phase plot containing a strange attractor, taken over a short period of time, of a region where unorganized activation patterns occur.

FIG. 18 is a counterpart plot 206D for atrial fibrillation data for a shorter sequence of 5 to 10 beats. As done for plot 206C in FIG. 17, the average cycle length is subtracted out for all beat n and beat n−1 measurements of cycle lengths, and FIG. 18 plots the difference in cycle lengths (n) (x-axis) against the difference in cycle length (n−1) (y-axis). The plot 206D thus centers the strange attractor dot around the axes intersection point 0,0. Plot 206D for an unorganized region shows a larger fuzzy dot around the origin, compared to plot 206C for an organized region.

When larger numbers of beats are to be analyzed, the processing element 204 can conduct a moving box-car average of the cycle lengths of 5–10 beats, to create a strange attractor centered on the origin.

Figure 19:
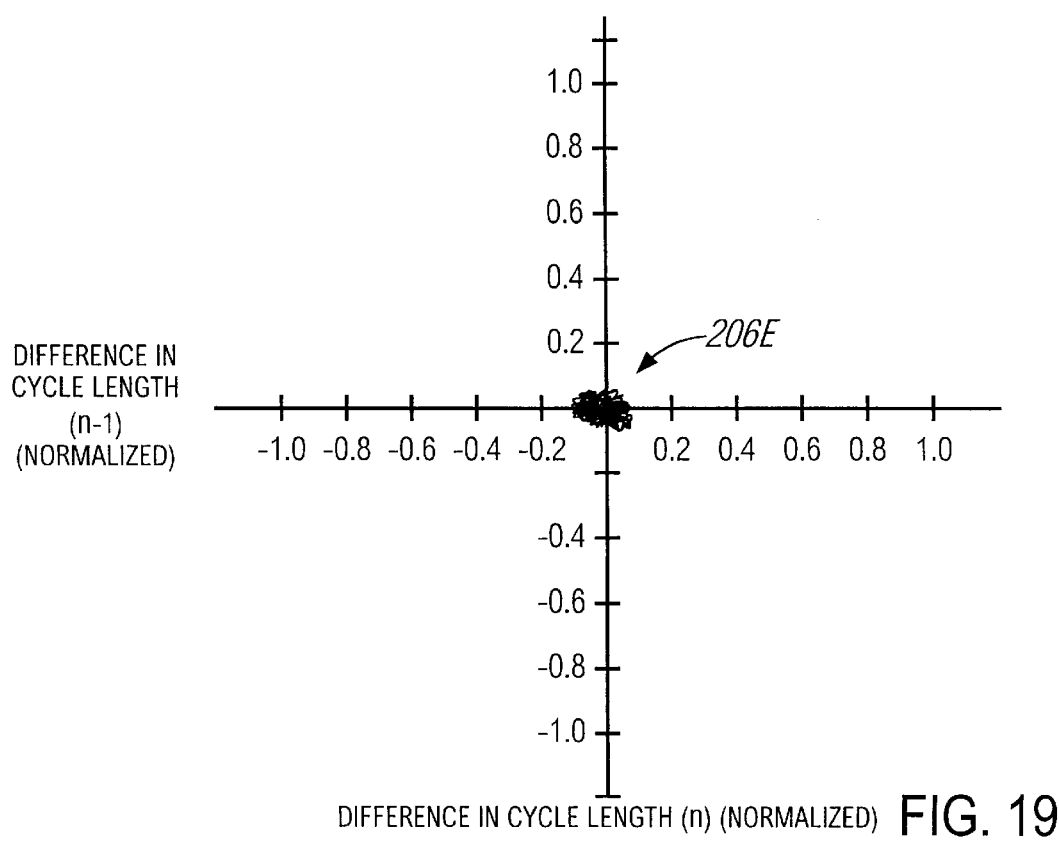
FIG. 19 is a representative normalized phase plot containing a strange attractor, taken over a short period of time, of a region where organized activation patterns occur.
Figure 20:
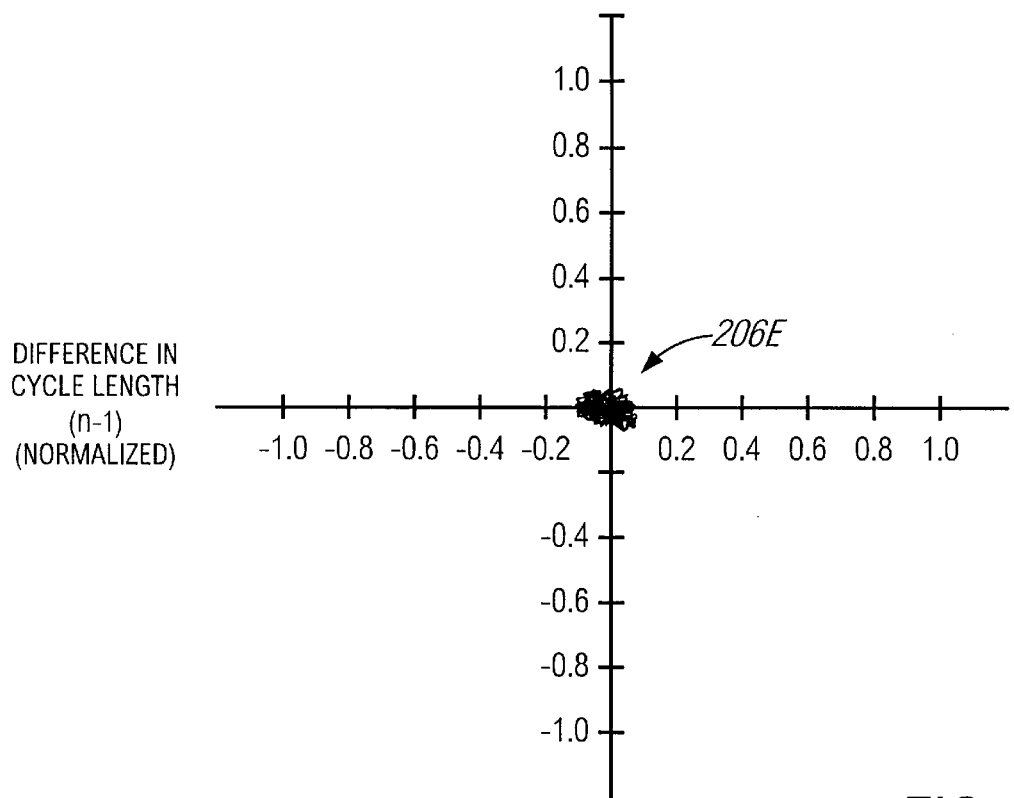
FIG. 20 is a representative normalized phase plot containing a strange attractor, taken over a short period of time, of a region where unorganized activation patterns occur.

In a preferred embodiment, the processing element 204 normalizes the cycle lengths by first subtracting an average cycle length, then dividing the resulting difference by the average cycle length. FIG. 19 shows a plot 206E processed in this fashion from data obtained from an organized region, wherein the difference in normalized cycle lengths (n) is plotted on the x-axis against the difference in normalized cycle length (n−1) on the y-axis. FIG. 20 shows a counterpart plot 206 F processed in this fashion from data obtained from an unorganized region. Again, the area of the strange attractor for the organized region (plot 206E in FIG. 19) is smaller than the area of the strange attractor for the unorganized region (plot 206F in FIG. 20). Normalizing the data provides a measure of the percentage variation in the cycle lengths of consecutive beats.

Referring to FIG. 21, the module 200 can further include an element 208, which analyses the size of the plotted fuzzy dot output 206. The relative size, or the relative change in size over time, indicates the level of rhythm organization at a single site, or over multiple sites.

A number of metrics can be used to determine the sizes of the fuzzy dots illustrated in FIGS. 17 to 20. Because the boundaries of the strange attractor are not always precisely defined, statistical measures of the size of the dot are appropriate. Such metrics include standard deviation of the distances of the dots from the origin, the average distance from the origin, and the median distance from origin. Other statistical or non-statistical metrics could be used. Other metrics of the consistency of consecutive cycle lengths can be directly applied to a set of data, including the standard deviation or covariance of the cycle lengths measured from one or more electrodes.

In a preferred embodiment, the organization module 200 is used in conjunction with the pacing algorithm 54, as FIG. 21 shows. In this embodiment (see FIG. 22), pacing is begun at multiple sites, with the objective being to organize multiple atrial regions within a given period of time. Multiple organized regions are then merged periodically to form larger combined regions of coordinated activity. Eventually, the merger of successively larger organized regions will encompass most or all the atria.

Figure 22:
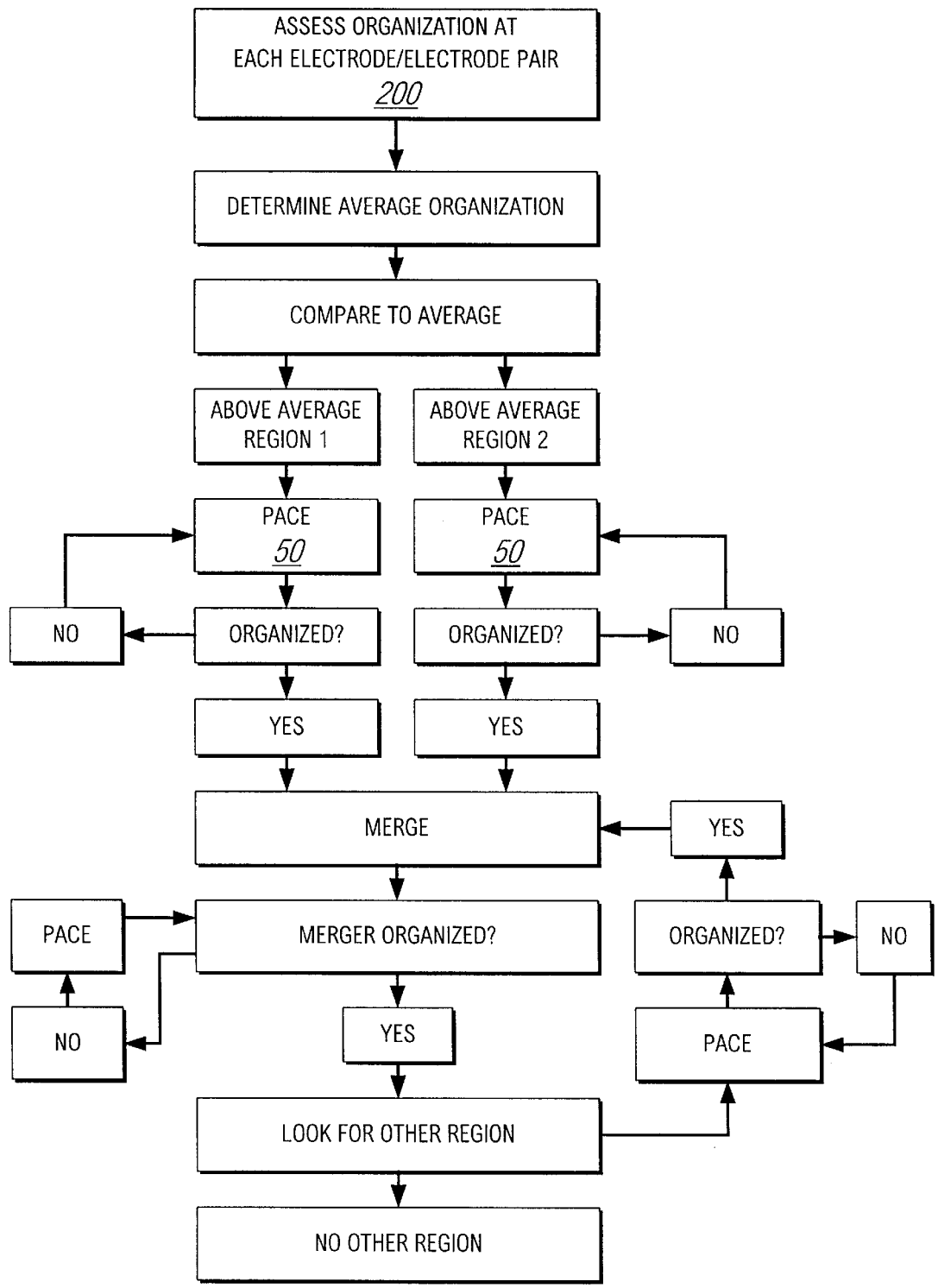
FIG. 22 is a flow chart showing an algorithm for defibrillating an atrial region using multiple electrodes.

As shown in FIG. 22, in carrying out the merger of multiple organized regions, the atrial fibrillation in a particular patient is assessed using the module 200. The targeted region can comprise one or both atria. The size of the strange attractor is measured from recordings at each electrode or electrode pair. The average extent of organization in the targeted atrial region is assessed by the module 200. Pacing using the algorithm 54 is begun, selecting first the multiple sites within the targeted atrial region which exhibit more organization than the average for the targeted region. For each of the local regions where the organization is above average, activity is monitored by the module 200, and additional pacing electrodes are added by the algorithm 54 as the activation pattern becomes more organized, based upon instantaneous analysis of the strange attractors.

The process is continued, using local decision-making criteria, until the borders of organized activity from at least two regions approach one another. When this occurs, the algorithm 54 seeks to coordinate the pacing sequences from the separate organized regions. As coordination is achieved, the regions are merged. The algorithm 54 treats the merged regions as a single region in terms of the pacing sequences for the combined sets of electrodes. When this hand-off procedure is done successfully, the separate regions of coordinated activity will merge into a large contiguous region. Large contiguous regions are merged in the same manner into larger continuous regions, until the entire targeted atrial region is organized.

In some patients it may be difficult, or even impossible, to organize the entire atria (all parts of the left and right atria) using pacing and organization schemes as above described. Even in those patients, however, partial organization of the atria provides an important benefit. Atria with more organized activity require much lower shock intensities to restore sinus rhythm (or other normal rate rhythm) than atria with less organized activity. By achieving some degree of regional organization by the methods previously described, a lower intensity shock can be delivered to completely organize the activity of the entire atria. Because some level of organization is possible, the intensity of the shock can be much lower in intensity than that usually required to defibrillate the atria (for example, on the order of 10-fold lower). This lower level of shock has a higher probability of being tolerated by a typical patient, than a typical defibrillation shock.

If the low level shock is unsuccessful, the pacing algorithm 54 is started immediately in conjunction with the module 200 to reestablish some degree of organization. If the physician believes that total organization is still possible with low level shock, another low level shock can be applied.

As FIG. 4 shows, two or more separate catheters (designated C1, C2, and C3 in FIG. 4), each carrying one or more electrodes 36, can be individually positioned within an atrium (the right atrium in FIG. 4) to together form a three-dimensional pattern of electrodes 36, approximating the pattern created by the composite three dimensional structure 20 shown in the left atrium in FIG. 4. The same pacing control algorithm 54 shown in FIG. 5 can be used to command the individual electrodes 36 to transmit pacing signals to defibrillate the atrium in the same manner already described. The three-dimensional assembled structure 20 of electrodes 30 (shown in FIG. 1) or the multi-catheter pattern of electrode 36 (shown in FIG. 4) can be located in a single atrium or located in both atria, as FIG. 4 shows, depending upon the clinical objectives.

The structure 20 and associated pacing control algorithm is adaptable to other diagnostic procedures.

For example, by using the structure 20 to pace and defibrillate in the right atrium, it can be determined if a given AF is right atrial dependent only (i.e., whether the left atrium is passively activated) In such cases, the possibility exists that therapeutic ablation to cure the AF may require only right atrial lesions, thereby preventing an unnecessary transseptal procedure, like that shown in FIG. 4 to position the structure 20.

The structure 20 and associated pacing control algorithm can also selectively pace along a selected path, which follows the patterns of electrodes 30 lying along a selected spline element 22. The pacing signals are transmitted simultaneously or sequentially through the electrodes 30 of single spline elements 22 until AF defibrillation occurs along a path. This technique identifies a localized path where AF defibrillation can be successfully obtained. The path thereby represents a candidate site for ablation, to create a long continuous lesion along the path, with the objective to permanently prevent reoccurrence of the AF.

In the illustrated and preferred embodiment, the pacing control algorithm 54 incorporates a pacing (first mode) protocol for reliably inducing atrial fibrillation with a defibrillation protocol in the second mode. The structure 20, which is positioned for use in the first mode as a part of an electrogram mapping procedure, also provides the platform for defibrillation in the second mode, without need to reposition the structure 20 or to deploy additional catheters. The structure 20, used in association with the pacing control algorithm 54, thereby facilitates numerous, successive arrhythmia induction and arrhythmia termination cycles, which are often necessary during cardiac diagnostic procedures.

The pacing control algorithm 54 may incorporate additional operating modes. For example, the algorithm may include an anti-bradycardia pacing mode, an anti-tachycardia pacing mode for termination of other types of arrhythmia (SVT's or VT's); a "shock" defibrillation mode capability for atrial and/or ventricular arrhythmias; and an synchronized electrogram storage mode.

Figure 7:
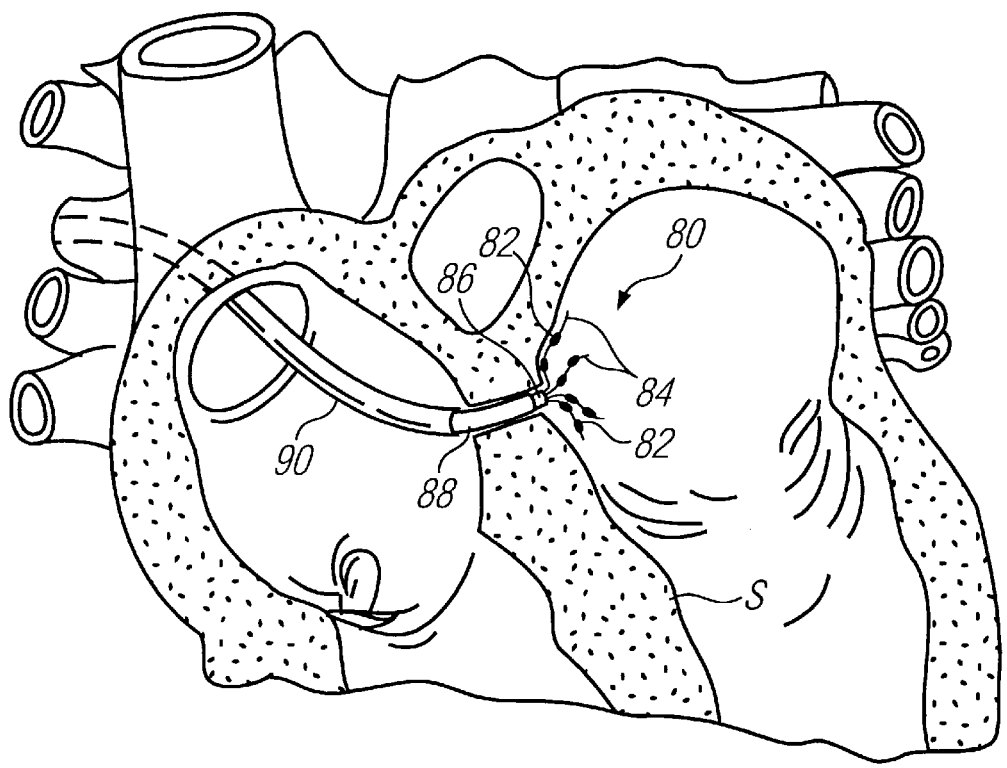
FIG. 7 is a side section view of a heart interior, shown in somewhat diagrammatic form, with a multiple electrode array positioned transeptally against the septal wall of the left atrium.
Figure 8:
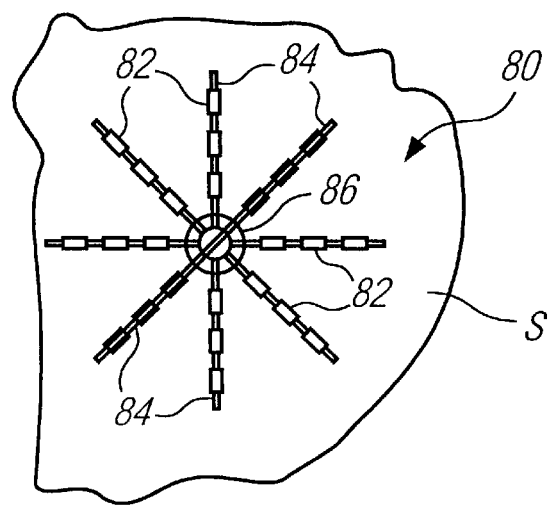
FIG. 8 is an end view of the multiple electrode array shown in FIG. 7.

The interatrial septum (identified by the letter S in FIG. 7) has been shown to be a junction for the propagation of atrial fibrillation wavelets. FIGS. 7 and 8 show a structure 80 adapted to locate multiple electrodes 82 against a large area of the interatrial septum (S). The structure 80 serves as the platform for delivering pacing signals or defibrillation shocks through the electrodes 82 to convert atrial fibrillation to sinus rhythm.

The structure 80 includes an array of spline elements 84 that radiate in a star-like pattern from the distal end 86 of a catheter tube 88 (as the end view in FIG. 8 best shows). Each spline element 84 carries multiple electrodes 82.

As shown in FIG. 7, the catheter tube 88 is deployed through a conventional transeptal sheath 90 into the left atrium. During introduction, the sheath 90 encloses the structure 80, maintaining the structure 80 in a collapsed condition, just as the sheath 44 collapses the structure 20 (see FIG. 3). Once located in the left atrium, the sheath 90 is pulled back past the septum S, and the spline elements 84, freed of the sheath 90, spring open. The physician pulls the catheter tube 88 back to bring the electrodes 82 into contact against the septal wall within the left atrium.

Figure 9:
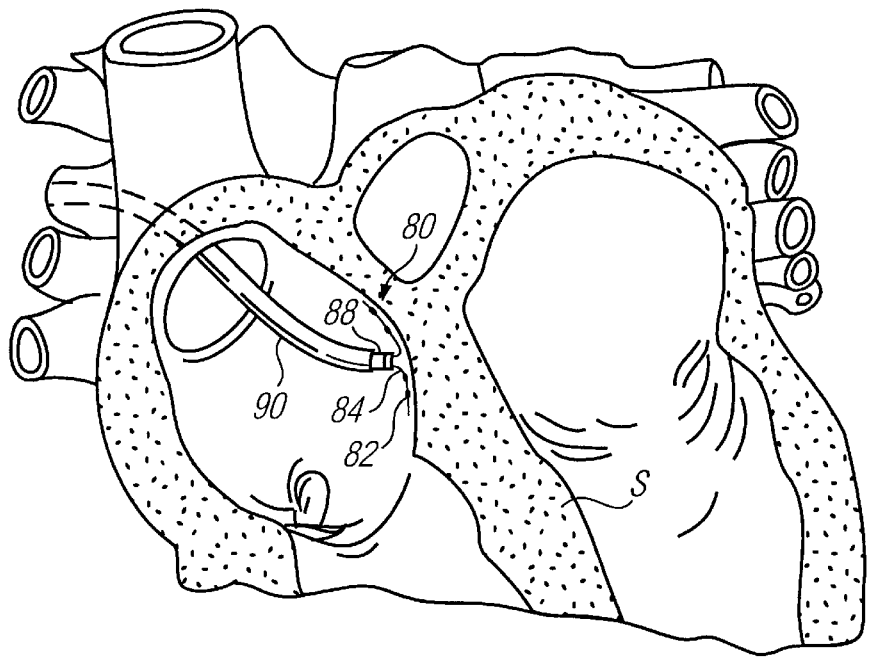
FIG. 9 is a side section view of a heart interior, shown in somewhat diagrammatic form, with the multiple electrode array shown in FIG. 8 positioned against the septal wall of the right atrium.

As FIG. 9 shows, the same structure 80 can be deployed in the right atrium by introduction through the sheath 90, previously described. Retraction of the sheath 90 allows the spline elements 84 to spring open. The physician pushes the catheter tube 88 toward the septum S to place the electrodes 82 into contact against the septal wall within the right atrium, as FIG. 8 shows.

Figure 10:
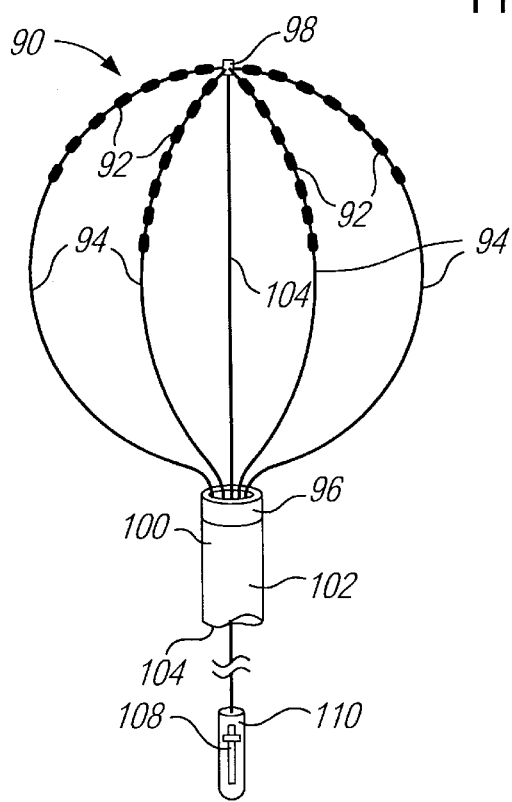
FIG. 10 is a side view of a structure carrying a high density array of electrodes at its distal end.
Figure 11:
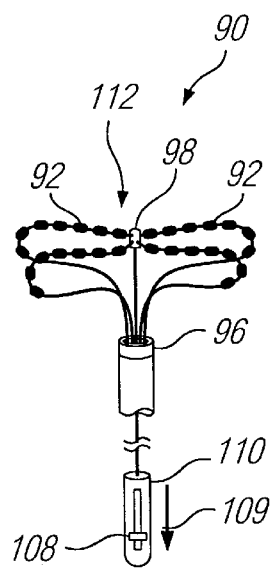
FIG. 11 is a side view of the structure shown in FIG. 10, with an associated stylet pulled proximally to create a generally flat distal surface for establishing large area contact between tissue and the high density array of electrodes.

FIGS. 10 and 11 show an alternative structure 90 for placing a high density array of electrodes 92 against the septal wall in the right atrium, or against another region anywhere within the heart. The structure 90 includes an array of spline elements 94 constrained between a proximal anchor 96 and a distal hub 98, like the structure 20 shown in FIG. 1. Like the structure 20, the structure 90 is attached to the distal end 100 of a catheter tube 102.

The spline elements 94 carry the electrodes 92. Unlike the pattern of electrodes 30 on the structure 20, the electrodes 92 on the structure 90 are concentrated in a high density pattern about the distal hub 98. Away from the distal hub 98, the spline elements 94 are free of electrodes 92.

A stylet 104 extends through the catheter tube bore 106 and is attached at its distal end to the distal hub 98. The proximal end of the stylet 104 is attached to a push-pull control mechanism 108 in the catheter tube handle 110. As FIG. 11 shows, pulling back on the mechanism 108 (arrow 109) draws the distal hub 98 toward the proximal anchor 96. The distal region of the spline elements 94 bend and deform outward, to form a generally planar surface 112 radiating about the distal hub 98, on which the electrodes 92 are located. The surface 112 presents the high density pattern of electrodes 92 for intimate surface contact with a large region of heart tissue.

In both the structure 20 shown in FIG. 1 and the structure 90 shown in FIGS. 10 and 11, the distal hub (respectively 24 and 98) can be made of an energy transmitting material and serve as an electrode, thereby increasing the electrode density.

The structures 80 (FIGS. 7 to 9) and 90 (FIGS. 10 and 11) can be used in association with the process controller 50, pacing module 52, and pacing control algorithm 54 as previously described and shown in FIG. 5. The control algorithm 64 commands the pacing module 52 to operate in the first mode to transmit to the electrodes 82 or 92 on the respective structures 80 or 90 pacing signals to induce atrial fibrillation. The control algorithm 64 also commands the pacing module 52 to operate in the second mode to transmit through the electrodes 82 or 92 pacing signals to capture and defibrillate the induced fibrillation.

Figure 6:
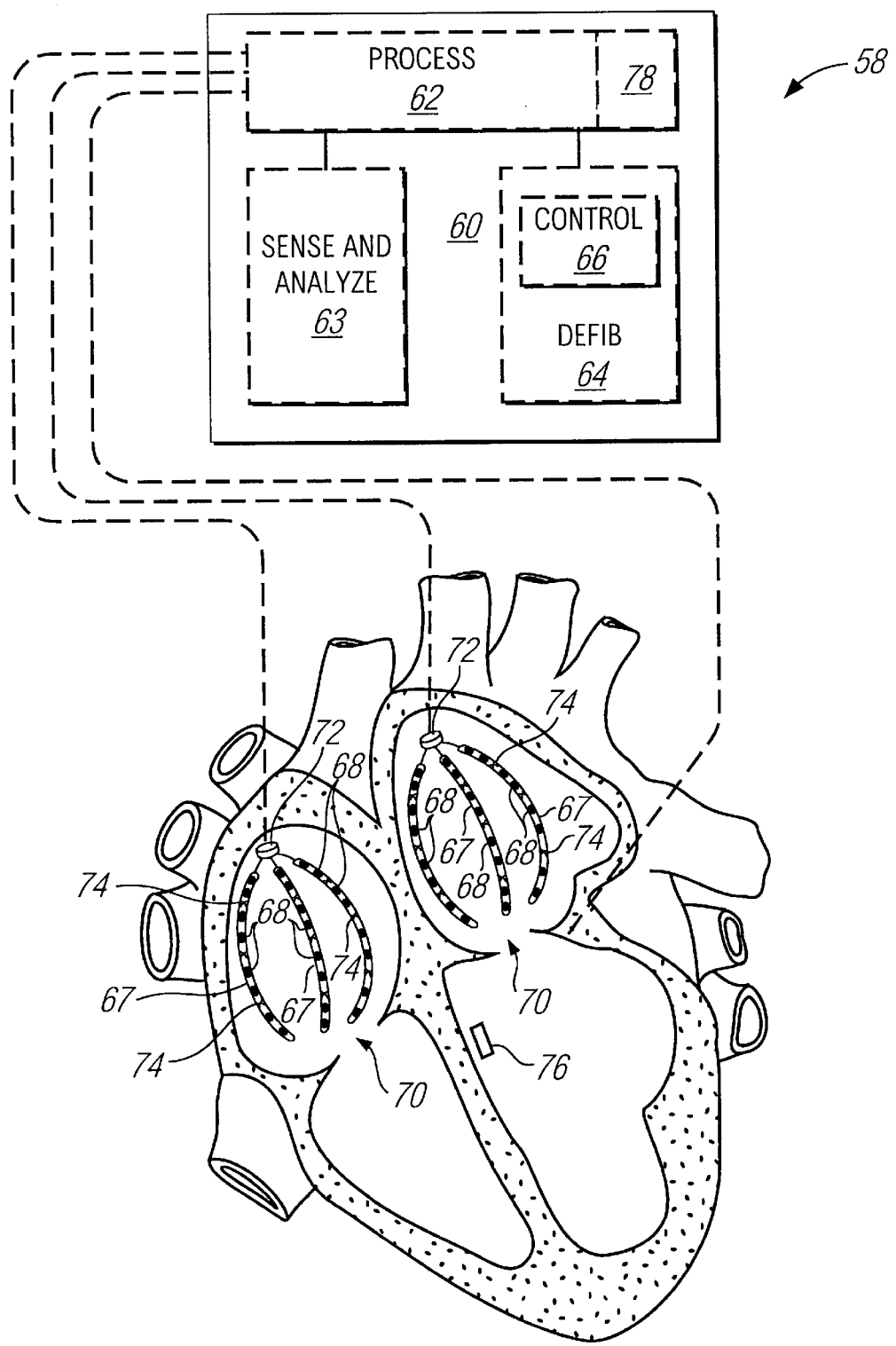
FIG. 6 is an enlarged, somewhat diagrammatic view of an implantable system intended to monitor and control cardiac activity, which includes an array of multiple electrodes located in the left and right atria to sense the occurrence of AF and to simultaneously transmit prescribed pacing signals to defibrillate the AF.

FIG. 6 shows another embodiment of the invention, which includes an implantable device 58. The device 58 comprises a small housing 60 made of an inert biocompatible material that can be implanted subpectorally in the body. The housing 60 encloses a processing element 62. The element 62 includes a sense and analyze module 63, which processes sensed electrical activity for the purpose of detecting abnormal electrical activity associated with arrhythmia in the atrium or ventricle. The processing element 62 also includes a defibrillation command module 64. The defibrillation command module 64 includes a control algorithm 66. A battery 78 serves as the power supply.

As shown in FIG. 6, one or more arrays 70 of electrodes 68 are coupled to the sense and analyze module 63 and the defibrillation command module 64. In the embodiment shown in FIG. 6, the electrode arrays 70 comprise flexible strips 67, which carry the electrodes 68. The electrodes 68 can take the form of solid rings, coils, deposited layers, alternate conducting structures, or any combination of such structures. The flexible strips 67 comprise lengths of memory wire enclosed in a biocompatible material.

The strips 67 are affixed to tissue within the heart using conventional implant fasteners 74. As shown in FIG. 6, for further stability, all or some of the strips 67 can be joined together at one end 72 to present a radiating pattern.

As FIG. 6 shows, the arrays 70 are affixed to the interior walls in both atria. Alternatively, the arrays 70 could be affixed to the interior walls of a single right or left atrium. The arrays 70 establish a three-dimensional grid of electrodes 68 in contact with a region of tissue spanning a majority of a given atrium. The arrays 70 are thereby functionally equivalent to the three-dimensional multiple structure 20 shown in FIG. 1. However, unlike the structure 20, which is intended for temporary residence within a heart chamber on the distal end of a catheter tube, the strips 68 are intended for longer term implantation in the heart.

A conventional electrode lead 76 is also coupled to the modules 63 and 64. As shown in FIG. 6, The distal tip of the electrode lead 76 is implanted in the right ventricle.

The device 68, the arrays 70, and the electrode lead 76 are implanted and electrically coupled together. The electrodes 68 on the arrays 70 and the electrode lead 76 continuously sense electrical activity for processing by the module 63 under the control of the processing module 62.

When the module 63 detects patterns of electric activity associated with a VT episode, the processing module 62 commands the algorithm 66 of the defibrillation module 64 to transmit conventional pacing signals to the right ventricle to terminate the VT.

When the module 63 detects patterns of electric activity associated with an AF episode, the processing module 62 commands the module 64, under the control of the algorithm 66, to transmit simultaneous or sequential multi-site pacing signals to the electrodes 68 on the arrays 70 to defibrillate the arrhythmia in the manner previously described.

Additionally, there could be one or more additional electrodes placed in one or multiple heart chambers for sensing or purposes other than defibrillation.

It should be appreciated that, instead of the multiple arrays of electrodes shown in FIG. 6, two or more conventional catheters/electrode leads may be positioned within an atrium to form a three-dimensional pattern of electrodes approximating the pattern created by the multiple electrode arrays.

Figure 12:
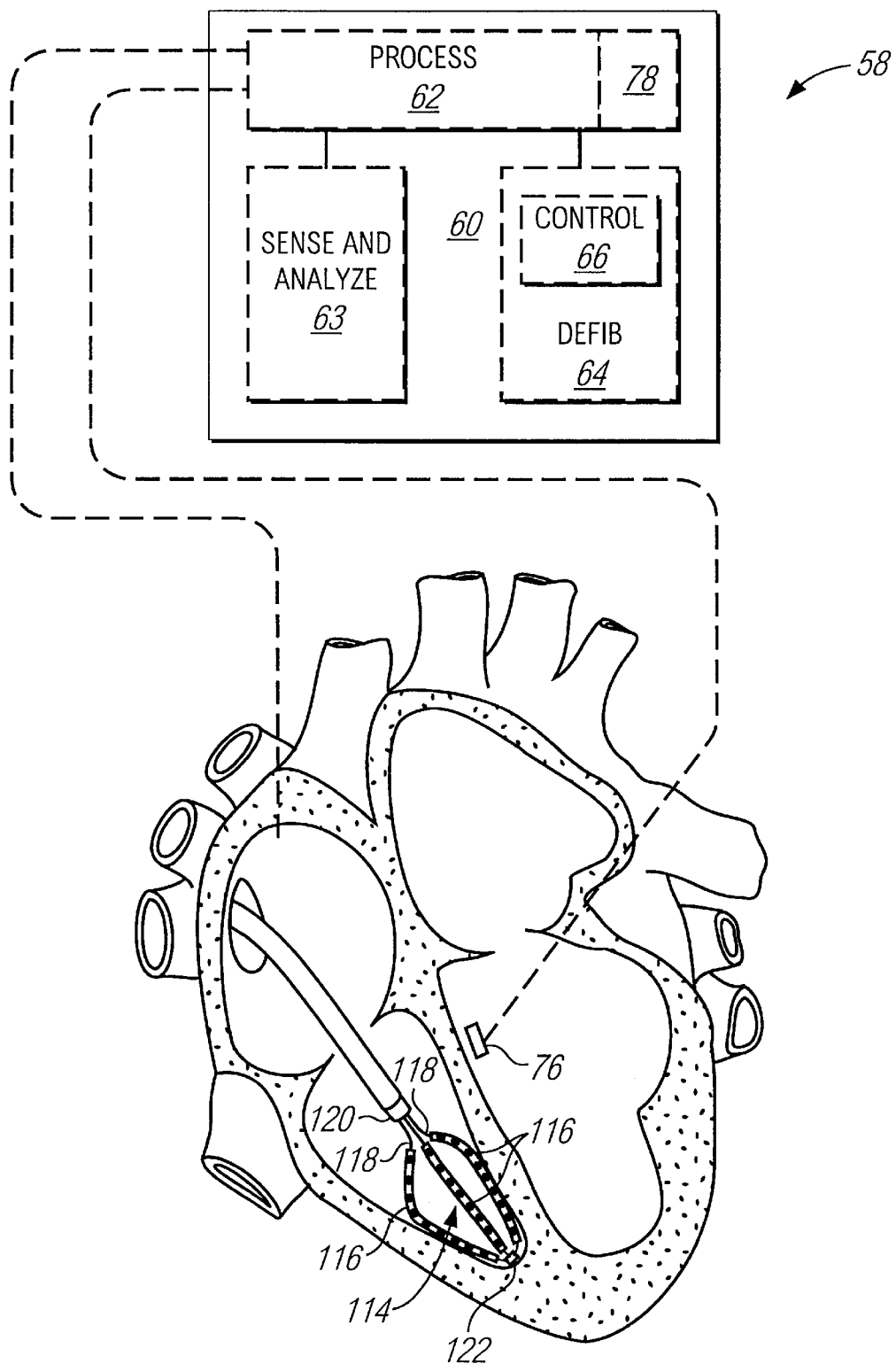
FIG. 12 is an enlarged, somewhat diagrammatic view of an implantable system intended to monitor and control cardiac activity, which includes a three-dimensional array of multiple electrodes implanted in the right ventricle.

FIG. 12 shows an alternative implantable structure 114 forming a three-dimensional pattern of electrodes 116. The structure 114 is like the structure 20 shown in FIG. 1, comprising an array of spline elements 118 constrained between a proximal anchor 120 and a distal hub 122. Each spline element 118 comprises a flexible body made from resilient, inert elastic memory material such as nickel titanium, having a diameter of about 4F to 7F. Each spline element 118 includes an outer, electrically nonconducting sleeve about which wire formed of platinum or stainless steel alloy is wound. The wound wire forms a continuous, elongated flexible electrode 116, which extends essentially along the entire length of the spline element 118.

The structure 114 can be implanted in either or both ventricles (FIG. 12 shows implantation in the right ventricle). As FIG. 12 shows, the electrodes 116 are coupled to the pectorally implanted sense and analyze module 63 and defibrillation command module 64 in the manner previously described and for the same purpose. The three-dimensional basket structure 114 shown in FIG. 12 assures good tissue contact and a uniform density distribution of electrodes 118 within the selected atrium. The structure 114 requires a relatively low defibrillation threshold, as the structure 114 distributes current about a relatively large surface area and requires relatively small capacitors to generate functional defibrillation pulses.

Figure 13:
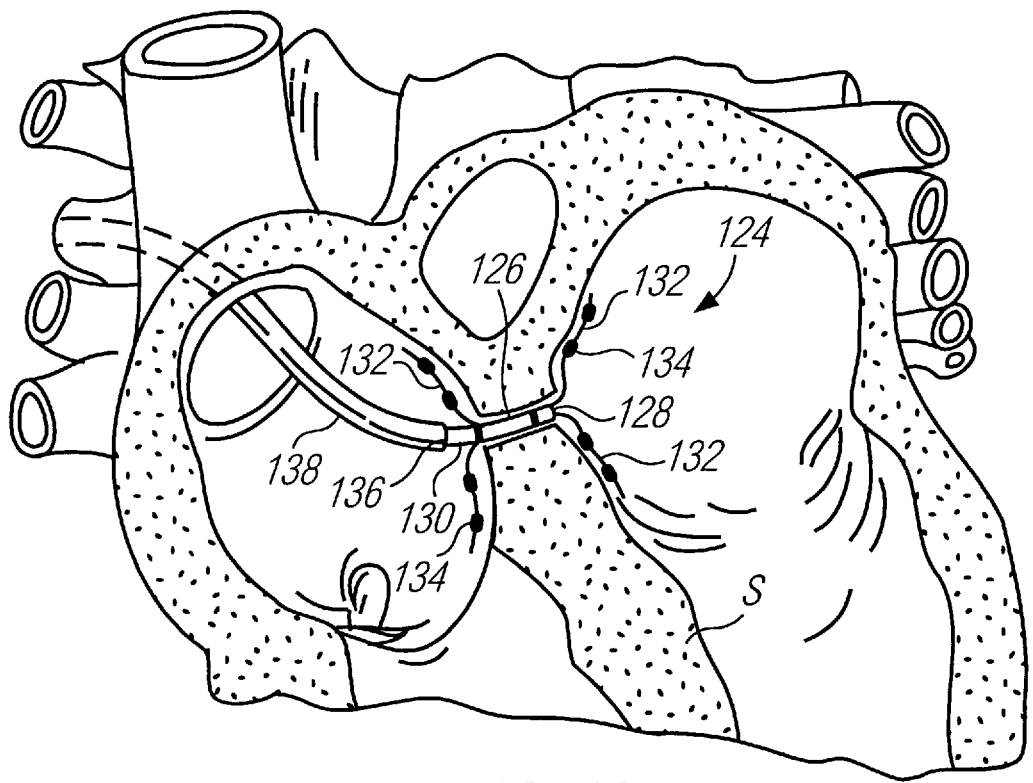
FIG. 13 is an enlarged, somewhat diagrammatic view of an implantable system intended to monitor and control cardiac activity, which includes an array of multiple electrodes located transeptally against the septal wall of the left and right atria.
Figure 14:
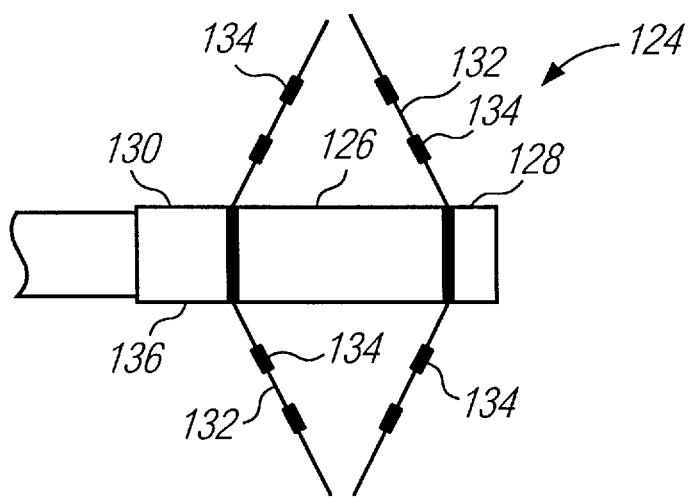
FIG. 14 is an enlarged side view of the multiple electrode array shown in FIG. 13, prior to implantation.

FIGS. 13 and 14 show an alternative implantable structure 124 suited for establishing high density electrode patterns on both sides of the septum. The structure 124 includes a body 126 having opposite ends 128 and 130. A set of splines 132 radiate in a star-like pattern from each end 128 and 130, in the same manner as previously shown and described in FIG. 8. The spline sets 132 are memory-biased toward the body 126 (as FIG. 14 shows). Each spline set 132 carries multiple electrodes 134.

The body 126 and attached lead 136 is introduced through a conventional transeptal sheath 138 through the septum S into the left atrium. During introduction, the sheath 138 encloses the structure 126, maintaining the spline sets 132 in a collapsed condition. Once located in the left atrium, the sheath 138 is pulled back past the septum S.

When freed of the sheath 138, the spline set 132 on the left atrium side spring open. The memory-bias hold the electrodes 134 against the septal wall within the left atrium.

Likewise, when freed of the sheath 138, the spline set 132 on the right atrium side spring open. The memory-bias holds the electrodes 134 against the septal wall within the right atrium.

The electrodes 134 are coupled to the pectorally implanted sense and analyze module 63 and defibrillation command module 64 in the manner previously described and for the same purpose. The structure 124 serves to continuously sense electrical activity and to transmit multiple site pacing signals to defibrillate an AF episode. The structure 124 also serves as to correct atrial-septal defects, while at the same time performing its sensing and defibrillation functions.

Features of the invention are set forth in the following claims.

We claim:

1. A system for assessing organization of heart rhythm in heart tissue comprising a monitoring element to sense electrical events in a heart tissue region and provide a sensed output, and a processing element coupled to the monitoring element to analyze the sensed output according to prescribed criteria and generate an organization-indicating output which varies in relation to organization of heart rhythm in the heart tissue region, wherein the monitoring element includes a spaced apart array of electrodes to monitor electrical events at spaced-apart areas in the heart tissue region.

2. A system according to claim 1 and further including a pacing module to deliver pacing pulses to the heart tissue region based, at least in part, upon the organization-indicating output.

3. A system for entraining heart tissue comprising a pacing module to deliver pacing pulses, a controller coupled to the pacing module operable to command the pacing module to deliver pacing pulses having selected pulse characteristics to a heart tissue region, a monitoring element to sense electrical events in the heart tissue region and provide a sensed output, a processing element coupled to the monitoring element to analyze the sensed outputs according to prescribed criteria and generate an organization-indicating output, which changes in relation to organization of heart rhythm in the heart tissue region, and the controller being constructed to alter the pulse characteristics based, at least in part, upon the organization-indicating output.

4. A system according to claim 3 wherein the controller also commands the pacing module to deliver pacing pulses having selected pulse characteristics to a second heart tissue region different than the first-mentioned heart region, wherein the monitoring element senses electrical events in both the first and second heart tissue regions and provides first and second sensed outputs, respectively, for the first and second heart regions, wherein the processing element analyzes the first and second sensed outputs according to prescribed criteria and generates first and second organization-indicating outputs, respectively, for the first and second heart regions, the first and second organization-indicating outputs changing in relation to organization of heart rhythm in the first and second heart tissue regions, respectively, and wherein the controller is constructed to alter the pulse characteristics based, at least in part, upon the first and second organization-indicating outputs.

5. A system according to claim 4 wherein the monitoring element includes multiple sensing electrodes in both the first and second heart regions.

6. A system according to claim 5 wherein the monitoring element senses electrical events at multiple electrodes in each of the first and second regions.

7. A system according to claim 5 wherein the monitoring element senses electrical events simultaneously at multiple electrodes in each of the first and second regions.

8. A system according to claim 1 or 3 wherein the processing element assesses variations in the organization-indication output over time.

9. A system according to claim 1 or 3 wherein the organization-indicating output is characterized by a geometric form that varies in relation to organization of heart rhythm in the heart tissue region.

10. A system according to claim 9 wherein the geometric form includes a plot of values derived from electrical events sensed in the heart tissue region.

11. A system according to claim 10 wherein the plot includes a strange attractor that varies in geometric form in relation to organization of heart rhythm in the heart tissue region.

12. A system according to claim 3 wherein the monitoring element includes multiple sensing electrodes.

13. A system according to claim 12 wherein the monitoring element includes a structure constructed to hold the multiple sensing electrodes in spaced apart relationship in association with the heart tissue region.

14. A system according to claim 13 wherein the monitoring element senses electrical events at multiple electrodes in the heart tissue region.

15. A system according to claim 14 wherein the monitoring element senses electrical events simultaneously at multiple electrodes in the heart tissue region.

16. A system according to claim 13 wherein the heart tissue region includes the interatrial septum.

17. A system according to claim 14 wherein the structure holds the multiple sensing electrodes in contact with the interatrial septum in a pattern that radiates from a common center.

18. A system according to claim 1 or 3 wherein the monitoring element senses activation cycles in the heart tissue region, and wherein the processing element correlates the activation cycles over a prescribed time period and generates the organization-indicating output based upon the correlation.

19. A system according to claim 1 or 3 wherein the monitoring element senses activation cycles in the heart tissue region, and wherein the processing element correlates the activation cycles over a prescribed time period by comparing one activation cycle length to a preceding activation cycle length and generates the organization-indicating output based upon the correlation.

20. A system according to claim 1 or 3 wherein the monitoring element senses activation cycles in the heart tissue region, and wherein the processing element generates the organization-indication output comprising a phase plot based upon the sensed activation cycles.

21. A system according to claim 1 or 3 wherein the monitoring element senses activation timing in the heart tissue region, and wherein the processing element generates the organization-indication output comprising a plot based upon the sensed activation timing.

22. A system according to claim 1 or 3 wherein the organization-indicating output comprises a plot based upon electrical events sensed in the heart tissue region, the plot comprising a geometric form that varies in relation to organization of heart rhythm in the heart tissue region.

23. A system according to claim 22 wherein the plot exhibits a first geometric form when heart rhythm in the heart tissue region is not substantially organized and a second geometric form, different than the first geometric form, when heart rhythm in the heart tissue region is substantially organized.

24. A system according to claim 22 wherein the processing element measures the geometric form of the plot and provides an output based upon the measurement.

25. A system according to claim 22 wherein the processing element assesses changes in the geometric form of the plot over time.

26. A system according to claim 22 wherein the geometric form includes a strange attractor.

27. A system according to claim 26 wherein the strange attractor has an effective area that varies in relation to organization of heart rhythm in the heart tissue region.

28. A system according to claim 27 wherein the processing element measures the effective area of the strange attractor and provides an output based upon the measurement.

29. A system according to claim 27 wherein the processing element assesses changes in the effective area of the strange attractor over time.

30. A method for entraining heart tissue comprising the steps of
delivering pacing pulses having selected pulse characteristics to a heart tissue region,
sensing electrical events in the heart tissue region,
analyzing the sensed electrical events to generate an organization-indicating output, which changes in relation to organization of heart rhythm in the heart tissue region, and
altering the pulse characteristics based, at least in part, upon the organization-indicating output.

31. A method according to claim 30 and further including the steps of
delivering pacing pulses having selected pulse characteristics to a second heart tissue region different than the first-mentioned heart region,
sensing electrical events in both the first and second heart tissue regions,
analyzing the sensed electrical events in the first and second heart tissue regions to generate, respectively, first and second organization-indicating outputs, the first and second organization-indicating outputs changing in relation to organization of heart rhythm in the first and second heart tissue regions, respectively, and altering the pulse characteristics based, at least in part, upon the first and second organization-indicating outputs.

32. A method according to claim 31
wherein the sensing step senses electrical events using multiple sensing electrodes in both the first and second regions.

33. A method according to claim 31
wherein the sensing step senses electrical events simultaneously at multiple electrodes in each of the first and second regions.

34. A method according to claim 30
and further including the step of assessing variations in the organization-indication output over time.

35. A method according to claim 30
wherein the organization-indicating output is characterized by a geometric form that varies in relation to organization of heart rhythm in the heart tissue region.

36. A system for entraining heart tissue comprising
a pacing module to generate pacing pulses, and
a controller coupling the pacing module to an array of electrodes held in association with a heart tissue region, the controller being operable in a local pacing mode to deliver pacing pulses to a first number of the electrodes, less than all the electrodes, to entrain a localized area within the heart tissue region, the controller also being operable in successive pacing modes to deliver pacing pulses to a successively greater number of the electrodes to entrain a successively larger area about the localized area.

37. A system according to claim 36
wherein the controller delivers pacing pulses having different pacing characteristics to electrodes within the number of electrodes.

38. A system according to claim 36
wherein the controller includes a monitoring element that senses heart electrical events in the localized area and generates an organization-indicating output, which varies in relation to organization of electrical events sensed within the localized area.

39. A system according to claim 38
wherein the controller delivers pacing pulses having different pacing characteristics to electrodes within the number of electrodes based, at least in part, upon the organization-indicating output.

40. A system according to claim 37 or 39
wherein the different pacing characteristics includes different pacing times at different electrodes within the number of electrodes.

41. A system according to claim 37 or 39
wherein the different pacing characteristics includes different pacing cycles at different electrodes within the number of electrodes.

42. A system according to claim 38
wherein the processing element assesses variations in the organization-indication output over time.

43. A system according to claim 38
wherein the organization-indicating output is characterized by a geometric form that varies in relation to organization of heart rhythm in the localized area.

44. A system according to claim 43
wherein the geometric form includes a plot of values derived from electrical events sensed in the localized area.

45. A system according to claim 43
wherein the plot includes a strange attractor that varies in geometric form in relation to organization of heart rhythm in the localized area.

46. A system according to claim 36
wherein the controller includes a processing element coupled to the electrodes that creates electrograms based upon electrical signals sensed in the localized area.

47. A system for entraining heart tissue comprising
multiple electrodes,
a structure constructed to hold the multiple electrodes in a spaced apart array in association with a heart tissue region,
a pacing module to generate pacing pulses, and
a controller coupling the pacing module to the array of electrodes held in association with a heart tissue region, the controller being operable in a local pacing mode to deliver pacing pulses to a first number of the electrodes, less than all the electrodes, to entrain a localized area within the heart tissue region, the controller also being operable in successive pacing modes to deliver pacing pulses to a successively greater number of the electrodes to entrain a successively larger area about the localized area.

48. A system according to claim 47
wherein the structure holds the multiple electrodes in a three-dimensional array.

49. A system according to claim 47 wherein the heart tissue region includes the interatrial septum.

50. A system according to claim 47
wherein the structure holds the multiple sensing electrodes in contact with the interatrial septum in a pattern that radiates from a common center.

51. A system for entraining heart tissue comprising
a pacing module to generate pacing pulses, and
a controller coupling the pacing module to an array of electrodes held in association with a heart tissue region, the controller being operable to deliver pacing pulses to a first number of the electrodes to entrain a first localized area within the heart tissue region, the controller also being operable to deliver pacing pulses to a second number of the electrodes to entrain a second localized area within the heart tissue region, the controller being further operative to merge the first and second localized areas into a combined area to entrain a larger area in the heart tissue region.

52. A system according to claim 51 wherein the controller delivers pacing pulses having different pacing characteristics to electrodes in the first and second localized areas.

53. A system according to claim 51
wherein the controller includes a monitoring element that senses heart electrical events in the first and second localized areas and generates a first organization-indicating output, which varies in relation to organization of electrical events sensed within the first localized area, and a second organization-indicating output, which varies in relation to organization of electrical events sensed within the second localized area.

54. A system according to claim 53
wherein the controller delivers pacing pulses having different pacing characteristics to electrodes in the first and second localized areas based, at least in part, upon the first and organization-indicating outputs, respectively.

55. A system according to claim 52 or 54 wherein the different pacing characteristics includes different pacing times at different electrodes in the first and second localized areas.

56. A system according to claim 52 or 54 wherein the different pacing characteristics includes different pacing cycles at different electrodes in the first and second localized areas.

57. A system according to claim 53 wherein the processing element assesses variations in the first and second organization-indication outputs over time.

58. A system according to claim 53 wherein the first and second organization-indicating outputs are each characterized by a geometric form that varies in relation to organization of heart rhythm in the respective first and second localized area.

59. A system according to claim 58 wherein the geometric form includes a plot of values derived from electrical events sensed in the respective first and second localized area.

60. A system according to claim 59 wherein the plot includes a strange attractor that varies in geometric form in relation to organization of heart rhythm in the respective first and second localized area.

61. A system according to claim 51 wherein the controller includes a processing element coupled to the electrodes that creates electrograms based upon electrical signals sensed in first and second localized areas.

62. A method for entraining heart tissue comprising
delivering pacing pulses to an array of electrodes held in association with a heart tissue region,
controlling the delivering step in a local pacing mode to deliver pacing pulses to a first number of the electrodes, less than all the electrodes, to entrain a localized area within the heart tissue region,
controlling the delivering step in successive pacing modes to deliver pacing pulses to a successively greater number of the electrodes to entrain a successively larger area about the localized area.

63. A method according to claim 62 wherein, in the first and second modes, the delivering step delivers pacing pulses having different pacing characteristics to electrodes within the number of electrodes.

64. A method according to claim 62 and further including the step of sensing heart electrical events in the localized area to generate an organization-indicating output, which varies in relation to organization of electrical events sensed within the localized area.

65. A method according to claim 64 wherein the delivering step delivers pacing pulses having different pacing characteristics to electrodes within the number of electrodes based, at least in part, upon the organization-indicating output.

66. A method according to claim 63 or 65 wherein the different pacing characteristics includes different pacing times at different electrodes within the number of electrodes.

67. A method according to claim 63 or 65 wherein the different pacing characteristics includes different pacing cycles at different electrodes within the number of electrodes.

68. A method according to claim 64 and further including a step assessing variations in the organization-indication output over time.

69. A method according to claim 64 wherein the organization-indicating output is characterized by a geometric form that varies in relation to organization of heart rhythm in the localized area.

70. A method for entraining heart tissue comprising the steps of
(i) delivering pacing pulses to an array of electrodes held in association with a heart tissue region,
(ii) controlling the delivering step (i) to deliver pacing pulses to a first number of the electrodes to entrain a first localized area within the heart tissue region,
(iii) controlling the delivering step (i) to deliver pacing pulses to a second number of the electrodes to entrain a second localized area within the heart tissue region, and
(iv) controlling the delivering step (i) to merge the first and second localized areas into a combined area to entrain a larger area in the heart tissue region.

71. A method according to claim 70 wherein the controlling steps (ii) and (iii) deliver pacing pulses having different pacing characteristics to the first and second localized areas.

72. A method according to claim 70 and further including the step of (v) sensing heart electrical events in the localized area to generate a first and second organization-indicating outputs, which vary in relation to organization of electrical events sensed within, respectively, the first and second localized areas.

73. A method according to claim 72 wherein the controlling steps (ii) and (iii) deliver pacing pulses having different pacing characteristics to the first and second localized areas based, at least in part, upon the first and second organization-indicating outputs, respectively.

74. A method according to claim 71 or 73 wherein the different pacing characteristics includes different pacing times at different electrodes within the number of electrodes.

75. A method according to claim 71 or 73 wherein the different pacing characteristics includes different pacing cycles at different electrodes within the number of electrodes.

76. A method according to claim 72 and further including a step assessing variations in the first and second organization-indication outputs over time.

77. A method according to claim 72 wherein the first and second organization-indicating outputs are each characterized by a geometric form that varies in relation to organization of heart rhythm in the respective first and second localized areas.

78. A system for defibrillating heart tissue in an atrium comprising
a monitoring element to sense electrical events in an atrial tissue region undergoing fibrillation and provide a sensed output,
a processing element coupled to the monitoring element to analyze the sensed output according to prescribed criteria and generate an organization-indicating output, which varies in relation to organization of heart rhythm in the atrial tissue region, the processing element including an assessor that assesses variations in the organization-indication output over time and generates a first status output when improvement in the organization of heart rhythm in the localized area is assessed, a pacing module to generate pacing pulses, and a controller coupling the pacing module to electrodes held in association with the atrial tissue region, the controller being operable to deliver pacing pulses having pulse characteristics selected to organize heart rhythm in at least a localized area within the atrial tissue region, and a defibrillation module constructed and arranged to deliver a low level defibrillation pulse of less than 1 Joule to the entire atrial tissue region upon generation of the first status output.

79. A system according to claim 78 wherein the organization-indicating output is characterized by a geometric form that varies in relation to organization of heart rhythm in the atrial tissue region.

80. A system according to claim 78 wherein the geometric form includes a plot of values derived from electrical events sensed in the atrial tissue region.

81. A system according to claim 79 wherein the plot includes a strange attractor that varies in geometric form in relation to organization of heart rhythm in the atrial tissue region.

82. A system according to claim 78 wherein the monitoring element includes a structure constructed to hold the electrodes in spaced apart relationship in association with the atrial tissue region.

83. A system according to claim 78 wherein the controller delivers pacing pulses having different pacing characteristics to the electrodes based, at least in part, upon the organization-indicating output.

84. A system according to claim 83 wherein the different pacing characteristics includes different pacing times at different electrodes within the number of electrodes.

85. A system according to claim 83 wherein the different pacing characteristics includes different pacing cycles at different electrodes within the number of electrodes.

86. A method for defibrillating heart tissue in an atrium comprising the steps of sensing electrical events in an atrial tissue region undergoing fibrillation, generating an organization-indicating output based upon the sensed electrical events, the organization-indicating output varying in relation to organization of heart rhythm sensed in the atrial tissue region, locating electrodes in association with the atrial tissue region, delivering pacing pulses to the electrodes, the pacing pulses having pulse characteristics selected to organize heart rhythm in at least a localized area within the atrial tissue region, assessing variations in the organization-indication output over time, and delivering a low level defibrillation pulse of less than 1 Joule to the entire atrial tissue when assessed variations indicate improvement in the organization of heart rhythm in the localized area.

87. A method according to claim 86 and further including the step of generating an organization-indicating output after delivering the low level defibrillation pulse to ascertain whether defibrillation of the atrial tissue region has been achieved.

88. A method according to claim 86 wherein the pacing pulses delivered to the electrodes have different pacing characteristics.

89. A method according to claim 88 wherein the different pacing characteristics are delivered based, at least in part, upon the organization-indicating output.

90. A method according to claim 88 wherein the different pacing characteristics includes different pacing times at different electrodes.

91. A method according to claim 88 wherein the different pacing characteristics includes different pacing cycles at different electrodes.

92. A system for identifying a candidate ablation site in heart tissue comprising a structure holding multiple electrodes along a localized path in association with a heart tissue region subject to fibrillation, a pacing module to generate pacing pulses, and a controller coupling the pacing module to the multiple electrodes to deliver pacing pulses only along the localized path, the controller including a monitoring element that senses electrical events along the localized path, and an identification component generating a candidate ablation site-identification output when the monitoring element senses defibrillation occurring along the localized path as a result of the pacing pulses.

93. A system according to claim 92 wherein the controller delivers pacing pulses in a first mode having first pulse characteristics to cause fibrillation in heart tissue along the localized path and delivers pacing pulses in a second mode having second pulse characteristics to entrain heart tissue along the localized path.

94. A system according to claim 92 wherein the controller delivers pacing pulses simultaneously to all electrodes along the localized path.

95. A system according to claim 92 wherein the controller delivers pacing pulses in a sequence to electrodes along the localized path.

96. A system according to claim 92 and further including a processing element coupled to the monitoring element to analyze the sensed electrical events according to prescribed criteria and generate an organization-indicating output, which varies in relation to organization of heart rhythm along the localized path.

97. A system according to claim 92 wherein the structure holds multiple electrodes along a first localized path and a second localized path in association with a heart tissue region subject to fibrillation, wherein the controller delivers pacing pulses along a selected one of the localized paths while the monitoring element senses electrical events along the selected localized path, and wherein the identification component generates a candidate ablation site-identification output specific to the selected localized path when the monitoring element senses defibrillation occurring along the selected localized path as a result of the pacing pulses.

98. A system according to claim 92
wherein the structure holds the electrodes in association with an interatrial septum.

99. A system according to claim 98
wherein the structure holds the electrodes in contact with the interatrial septum in a pattern that radiates from a common center.

100. A system according to claim 92
and further including an ablation element to create a lesion pattern along the localized path.

101. A method for identifying a candidate ablation site in heart tissue comprising the steps of holding multiple electrodes along a localized path in association with a heart tissue region subject to fibrillation, delivering pacing pulses only along the localized path, sensing electrical events along the localized path, and generating a candidate ablation site-identification output when the monitoring element senses defibrillation occurring along the localized path as a result of the pacing pulses.

102. A method according to claim 101
wherein the delivering step delivers pacing pulses in a first mode having first pulse characteristics to cause fibrillation in heart tissue along the localized path and delivers pacing pulses in a second mode having second pulse characteristics to entrain heart tissue along the localized path.

103. A method according to claim 101
wherein the delivering step delivers pacing pulses simultaneously to all electrodes along the localized path.

104. A method according to claim 101
wherein the delivering step delivers pacing pulses in a sequence to electrodes along the localized path.

105. A method according to claim 101
and further including a step of analyzing the sensed electrical events according to prescribed criteria and generate an organization-indicating output, which varies in relation to organization of heart rhythm along the localized path.

106. A method according to claim 101
wherein the holding step includes holding multiple electrodes along a first localized path and a second localized path in association with a heart tissue region subject to fibrillation, wherein the delivering step delivers pacing pulses along a selected one of the localized paths while the sensing step senses electrical events along the selected localized path, and wherein the generating step generates a candidate ablation site-identification output specific to the selected localized path when the sensing step senses defibrillation occurring along the selected localized path as a result of the pacing pulses.

107. A method according to claim 108
wherein the holding step holds the electrodes in association with an interatrial septum.

108. A method according to claim 101
and further including creating a lesion pattern along the localized path identified by the generation of the candidate ablation site-identification output.

* * * * *